(12) United States Patent
Nakai et al.

(10) Patent No.: US 11,845,247 B2
(45) Date of Patent: Dec. 19, 2023

(54) COMPOSITION FOR LAMINATED MATERIAL USED FOR MEDICAL LUBRICATING MEMBER, LAMINATED MATERIAL USED FOR MEDICAL LUBRICATING MEMBER, MEDICAL LUBRICATING MEMBER, MEDICAL DEVICE, AND METHOD FOR PRODUCING LAMINATED MATERIAL USED FOR MEDICAL LUBRICATING MEMBER

(71) Applicant: FUJIFILM Corporation, Tokyo (JP)

(72) Inventors: Yoshihiro Nakai, Ashigarakami-gun (JP); Sotaro Inomata, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 239 days.

(21) Appl. No.: 17/147,611

(22) Filed: Jan. 13, 2021

(65) Prior Publication Data

US 2021/0129509 A1    May 6, 2021

Related U.S. Application Data

(63) Continuation of application No. PCT/JP2019/028029, filed on Jul. 17, 2019.

(30) Foreign Application Priority Data

Jul. 17, 2018    (JP) ................. 2018-134504

(51) Int. Cl.
*B32B 27/28*    (2006.01)
*B32B 27/08*    (2006.01)
(Continued)

(52) U.S. Cl.
CPC ............ *B32B 27/283* (2013.01); *B32B 27/08* (2013.01); *B32B 27/20* (2013.01); *B32B 27/26* (2013.01);
(Continued)

(58) Field of Classification Search
CPC ....... B32B 27/08; B32B 27/26; B32B 27/302; B32B 27/308; B32B 27/34; B32B 2250/02; B32B 2250/03; B32B 2250/24
See application file for complete search history.

(56) References Cited

U.S. PATENT DOCUMENTS

8,158,695 B2 * 4/2012 Vanderlaan ............. A61L 27/18
523/113
2002/0128419 A1    9/2002 Terry et al.
(Continued)

FOREIGN PATENT DOCUMENTS

CN    1771064 A    5/2006
CN    101528281 A    9/2009
(Continued)

OTHER PUBLICATIONS

Notice of Reasons for Refusal dated Aug. 17, 2021 by the Japanese Patent Office in Japanese Application No. 2020-531332.
(Continued)

*Primary Examiner* — Michael C Miggins
(74) *Attorney, Agent, or Firm* — Sughrue Mion, PLLC

(57) ABSTRACT

There is provided a composition for a laminated material used for a medical lubricating member, the composition including a polymer b including a polysiloxane structure, a catalyst for crosslinking reaction, and a crosslinking agent having a particular structure. The polymer b includes at least one of an acrylic acid component, an acrylic acid ester component, an acrylamide component, or a styrene component and has a hydroxy group, a carboxy group, an amino group, an isocyanate group, an oxazolinyl group, an epoxy group, a vinyl group, an ethynyl group, a sulfanyl group, an azide group, a trialkoxysilyl group, or an acid anhydride structure. There are also provided a laminated material and a medical lubricating member produced from the composition, a medical device including the laminated material and
(Continued)

the medical lubricating member, and a method for producing the laminated material and the medical lubricating member.

3 Claims, 1 Drawing Sheet

(51) Int. Cl.
*B32B 27/20* (2006.01)
*B32B 27/26* (2006.01)
*B32B 27/30* (2006.01)
*B32B 27/34* (2006.01)
*B32B 27/36* (2006.01)

(52) U.S. Cl.
CPC .......... *B32B 27/302* (2013.01); *B32B 27/308* (2013.01); *B32B 27/34* (2013.01); *B32B 27/36* (2013.01); *B32B 2250/02* (2013.01); *B32B 2250/03* (2013.01); *B32B 2250/24* (2013.01); *B32B 2307/746* (2013.01); *B32B 2325/00* (2013.01); *B32B 2333/08* (2013.01); *B32B 2377/00* (2013.01); *B32B 2383/00* (2013.01); *B32B 2535/00* (2013.01)

(56) References Cited

U.S. PATENT DOCUMENTS

| | | |
|---|---|---|
| 2004/0209784 A1 | 10/2004 | Hardamn et al. |
| 2006/0193894 A1* | 8/2006 | Jen .................... C08J 7/0427 427/2.24 |
| 2008/0071228 A1 | 3/2008 | Wu et al. |
| 2019/0328931 A1 | 10/2019 | Inomata et al. |

FOREIGN PATENT DOCUMENTS

| | | |
|---|---|---|
| EP | 2 522 375 A1 | 11/2012 |
| JP | 1-319518 A | 12/1989 |
| JP | 4-175309 A | 6/1992 |
| JP | 2002-529170 A | 9/2002 |
| JP | 2009-261437 A | 11/2009 |
| JP | 2012-121998 A | 6/2012 |
| JP | 2014-105325 A | 6/2014 |
| WO | 2009/119690 A1 | 10/2009 |
| WO | 2018/131518 A1 | 7/2018 |

OTHER PUBLICATIONS

International Search Report dated Sep. 10, 2019, issued by the International Searching Authority in application No. PCT/JP2019/028029.

Written Opinion dated Sep. 10, 2019, issued by the International Searching Authority in application No. PCT/JP2019/028029.

English translation of the International Preliminary Report on Patentability (Chapter II of the Patent Cooperation Treaty) dated Jan. 17, 2021, issued in application No. PCT/JP2019/028029.

Communication dated Nov. 3, 2021 from the China National Intellectual Property Administration in corresponding Application No. 201980043294.7.

Extended European Search Report dated Aug. 18, 2021 from the European Patent Office in corresponding EP Application No. 19838057.8.

* cited by examiner

COMPOSITION FOR LAMINATED MATERIAL USED FOR MEDICAL LUBRICATING MEMBER, LAMINATED MATERIAL USED FOR MEDICAL LUBRICATING MEMBER, MEDICAL LUBRICATING MEMBER, MEDICAL DEVICE, AND METHOD FOR PRODUCING LAMINATED MATERIAL USED FOR MEDICAL LUBRICATING MEMBER

CROSS-REFERENCE TO RELATED APPLICATIONS

This application is a Continuation of PCT International Application No. PCT/JP2019/028029 filed on Jul. 17, 2019, which claims priority under 35 U.S.C. § 119 (a) to Japanese Patent Application No. 2018-134504 filed in Japan on Jul. 17, 2018. Each of the above applications is hereby expressly incorporated by reference, in its entirety, into the present application.

BACKGROUND OF THE INVENTION

1. Field of the Invention

The present invention relates to a composition for laminated materials used for medical lubricating members, a laminated material used for medical lubricating members, a medical lubricating member, a medical device, and a method for producing a laminated material used for medical lubricating members.

2. Description of the Related Art

Medical devices that are inserted into or applied to blood vessels, the trachea, the digestive tract, or other body cavities or tissues in order to examine or treat the human body are required not to cause tissue damage or inflammation upon contact with the tissue. In order to produce such a medical device, a composition containing a silicone compound is used. For example, JP1989-319518A (JP-H1-319518A) describes, as the composition containing a silicone compound, a composition containing, as a main component, a linear silicone/acrylic copolymer obtained by polymerizing a silicone having a radically polymerizable group, a (meth)acrylic acid ester, and a carboxy group-containing monoethylenically unsaturated monomer.

SUMMARY OF THE INVENTION

When a medical device is used in contact with a body tissue, high friction between the medical device and a surface of the tissue damages the tissue. For example, an endoscope is used by being slid in a body cavity, and therefore it is important to improve the slidability of a surface member that comes into contact with a tissue in a body cavity. This requires the uniformity of the properties, thickness, and the like of the surface member. Since the inside of the body cavity is in a wet state, the surface member of the medical device is required to have high slidability particularly in a wet state.

In some cases, a medical tube is inserted into a body cavity, and a camera, a jig, or the like is inserted into the tube while water is being passed through the tube to observe the inside of the body cavity or to take a biopsy. Therefore, the slidability between the surface member provided on the inner wall of the tube and the jig needs to be improved in a wet state.

Furthermore, the medical device or its constituent components may be subjected to high-curvature bending. Therefore, the surface member of the medical device is required to have characteristics (bending resistance) in which cracking is less likely to occur even when the surface member is bent.

Since the medical device is sterilized by dry heat sterilization, ethylene oxide gas sterilization, or the like or disinfected with a chemical solution for repeated use, the surface member of the medical device is also required to have heat resistance or chemical resistance.

From the viewpoint of prolonging the service life of the medical device, the surface member of the medical device is required not to be easily peeled off from the medical device (to have excellent adhesiveness to a substrate).

However, the technique disclosed in JP1989-319518A (JP-H01-319518A) does not sufficiently satisfy the above characteristics.

It is an object of the present invention to provide a composition and a laminated material capable of providing a medical lubricating member that includes a surface member disposed on a substrate and having a uniform thickness, that is excellent in terms of slidability in a wet state, that is also excellent in terms of bending resistance, heat resistance, and chemical resistance, and that is also excellent in terms of adhesiveness between the surface member and the substrate. It is another object of the present invention to provide a medical lubricating member that includes a layer disposed on a substrate and having a uniform thickness, that is excellent in terms of slidability in a wet state, that is also excellent in terms of bending resistance, heat resistance, and chemical resistance, and that is also excellent in terms of adhesiveness between a surface member and the substrate. It is another object of the present invention to provide a medical device including the above medical lubricating member. It is another object of the present invention to provide a method for producing the above laminated material and the above medical lubricating member.

The above objects have been achieved by the following means.

<1>

A composition for a laminated material used for a medical lubricating member includes a polymer b including a polysiloxane structure, a catalyst for crosslinking reaction, and a crosslinking agent.

The polymer b includes, as a constituent component, at least one of an acrylic acid component, an acrylic acid ester component, an acrylamide component, or a styrene component. The polymer b has at least one of a hydroxy group, a carboxy group, an amino group, an isocyanate group, an oxazolinyl group, an epoxy group, a vinyl group, an ethynyl group, a sulfanyl group, an azide group, a trialkoxysilyl group, or an acid anhydride structure.

The crosslinking agent includes at least one of a crosslinking agent having a structural unit represented by formula (CL1) below or a crosslinking agent represented by formula (CL2) below.

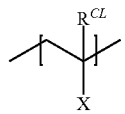

Formula (CL1)

Formula (CL2)

$Y \!\!-\!\![R^{dm}]_m$

In the formulae, $R^{CL}$ represents a hydrogen atom or an organic group. X represents a hydroxy group, a carboxy group, an amino group, an isocyanate group, an oxazolinyl group, an epoxy group, a vinyl group, an ethynyl group, a sulfanyl group, an azide group, a trialkoxysilyl group, or a group having an acid anhydride structure.

Y represents an m-valent linking group, and m represents an integer of 2 or more. $R^{dm}$ has the same definition as X.

<2>

A laminated material used for a medical lubricating member includes a substrate a and a layer b disposed on the substrate a. The layer b includes a catalyst for crosslinking reaction and a crosslinked polymer including, as a constituent component, a polymer b including a polysiloxane structure.

The polymer b includes, as a constituent component, at least one of an acrylic acid component, an acrylic acid ester component, an acrylamide component, or a styrene component. The polymer b has at least one of a hydroxy group, a carboxy group, an amino group, an isocyanate group, an oxazolinyl group, an epoxy group, a vinyl group, an ethynyl group, a sulfanyl group, an azide group, a trialkoxysilyl group, or an acid anhydride structure.

The crosslinked polymer has a crosslinking agent component including at least one of a crosslinking agent having a structural unit represented by formula (CL1) below or a crosslinking agent represented by formula (CL2) below.

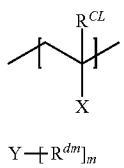

Formula (CL1)

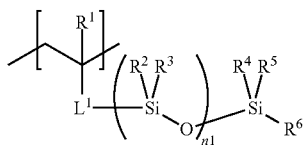

Formula (CL2)

In the formulae, $R^{CL}$ represents a hydrogen atom or an organic group. X represents a hydroxy group, a carboxy group, an amino group, an isocyanate group, an oxazolinyl group, an epoxy group, a vinyl group, an ethynyl group, a sulfanyl group, an azide group, a trialkoxysilyl group, or a group having an acid anhydride structure.

Y represents an m-valent linking group, and m represents an integer of 2 or more. $R^{dm}$ has the same definition as X.

<3>

In the laminated material used for a medical lubricating member according to <2>, the layer b includes at least one of a filler, a film-forming aid, or a viscosity modifier.

<4>

In the laminated material used for a medical lubricating member according to <2> or <3>, the polymer b is a graft polymer having the polysiloxane structure in a graft chain.

<5>

In the laminated material used for a medical lubricating member according to any one of <2> to <4>, the polymer b includes a structural unit represented by formula (1) below and includes at least one of a structural unit represented by formula (2) below, a structural unit represented by formula (3) below, or a structural unit represented by formula (4) below.

Formula (1)

In the formula, $R^1$ to $R^6$ represent a hydrogen atom or an organic group. $L^1$ represents a single bond or a divalent linking group, and n1 represents 3 to 10,000.

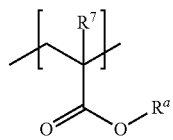

Formula (2)

In the formula, $R^7$ and $R^a$ represent a hydrogen atom or an organic group.

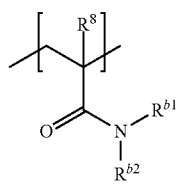

Formula (3)

In the formula, $R^8$, $R^{b1}$, and $R^{b2}$ represent a hydrogen atom or an organic group.

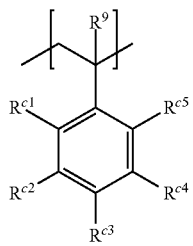

Formula (4)

In the formula, $R^9$ represents a hydrogen atom or an organic group. $R^{c1}$ to $R^{c5}$ represent a hydrogen atom, a halogen atom, or an organic group.

<6>

In the laminated material used for a medical lubricating member according to <5>, $R^a$ represents a group represented by formula (5) below or a nitrogen-containing organic group.

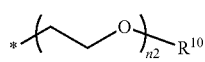

Formula (5)

In the formula, n2 represents 1 to 10,000. $R^{10}$ represents a hydrogen atom or an organic group, and * represents a bonding site.

<7>

In the laminated material used for a medical lubricating member according to <5> or <6>, n1 represents 135 to 10,000.

<8>

In the laminated material used for a medical lubricating member according to any one of <2> to <7>, the catalyst for crosslinking reaction includes at least one of a blocked acid, sulfonic acid, phosphate acid, Lewis acid, or carboxylic acid.

<9>

In the laminated material used for a medical lubricating member according to <3>, the filler includes at least one of silicon, aluminum, titanium, zirconium, zinc, tin, iron, an oxide thereof, or a hydrolytic condensation product of the oxide.

<10>

In the laminated material used for a medical lubricating member according to <3> or <9>, the film-forming aid includes at least one of an anionic surfactant, a nonionic surfactant, a polyether-modified siloxane, or a silicone oil.

<11>

In the laminated material used for a medical lubricating member according to any one of <3>, <9>, and <10>, the viscosity modifier includes at least one of a cellulose-based viscosity modifier, a polycarboxylic acid-based viscosity modifier, a polyethylene glycol-based viscosity modifier, a water-soluble polymer-based viscosity modifier, or a smectite-based viscosity modifier.

<12>

In the laminated material used for a medical lubricating member according to any one of <2> to <11>, the substrate a is formed of at least one of a urethane resin, a silicone resin, a fluorocarbon resin, an olefin resin, or an acrylic resin.

<13>

In the laminated material used for a medical lubricating member according to any one of <2> to <12>, the medical lubricating member is used as a member of a medical device selected from the group consisting of a medical tube, a guide wire, an endoscope, a surgical needle, a surgical suture, forceps, an artificial blood vessel, an artificial heart, and a contact lens.

<14>

A medical lubricating member has the laminated material used for a medical lubricating member according to any one of <2> to <12> and a layer c that is disposed on the layer b constituting the laminated material and that includes a hydrophilic polymer.

<15>

A medical device includes the medical lubricating member according to <14>, wherein the medical device is selected from the group consisting of a medical tube, a guide wire, an endoscope, a surgical needle, a surgical suture, forceps, an artificial blood vessel, an artificial heart, and a contact lens.

<16>

A method for producing a laminated material used for a medical lubricating member and having a substrate a and a layer b disposed on the substrate a includes a step of forming the layer b by applying, onto the substrate a, a composition including a polymer b including a polysiloxane structure, a catalyst for crosslinking reaction, and a crosslinking agent.

The polymer b includes, as a constituent component, at least one of an acrylic acid component, an acrylic acid ester component, an acrylamide component, or a styrene component. The polymer b has at least one of a hydroxy group, a carboxy group, an amino group, an isocyanate group, an oxazolinyl group, an epoxy group, a vinyl group, an ethynyl group, a sulfanyl group, an azide group, a trialkoxysilyl group, or an acid anhydride structure.

The crosslinking agent includes at least one of a crosslinking agent having a structural unit represented by formula (CL1) below or a crosslinking agent represented by formula (CL2) below.

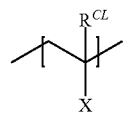

Formula (CL1)

Formula (CL2)

In the formulae, $R^{CL}$ represents a hydrogen atom or an organic group. X represents a hydroxy group, a carboxy group, an amino group, an isocyanate group, an oxazolinyl group, an epoxy group, a vinyl group, an ethynyl group, a sulfanyl group, an azide group, a trialkoxysilyl group, or a group having an acid anhydride structure.

Y represents an m-valent linking group, and m represents an integer of 2 or more. $R^{dm}$ has the same definition as X.

<17>

A method for producing a medical lubricating member includes obtaining a laminated material by the method for producing a laminated material used for a medical lubricating member according to <16> and forming a layer c including a hydrophilic polymer on the layer b of the laminated material.

In this specification, every numerical range expressed using "to" means a range including numerical values before and after "to" as the lower and upper limits.

In this specification, when a plurality of substituents and linking groups are represented by a particular symbol and a plurality of structural units having substituents and linking groups are represented by a particular symbol (hereafter referred to as substituents and the like), or when a plurality of substituents and the like are simultaneously or alternatively defined, the substituents and the like may be the same as or different from each other. The same also applies to the definition of the number of substituents and the like. When a plurality of substituents and the like are close (particularly adjacent) to each other, they may be linked or fused to each other to form a ring.

In this specification, unless otherwise specified, the form of polymers is not particularly limited, and may be any form such as random, block, or graft as long as the effects of the present invention are not impaired.

In this specification, the terminal structure of polymers is not particularly limited. The terminal structure is appropriately determined in accordance with the type of substrate used during synthesis, the type of quenching agent (reaction terminator) during synthesis, and the like, and is not uniquely determined. Examples of the terminal structure include a hydrogen atom, a hydroxy group, a halogen atom, an ethylenically unsaturated group, and an alkyl group.

In this specification, the terms "acrylic acid", "acrylamide", and "styrene" are used in a broader sense than usual.

That is, the term "acrylic acid" refers to all compounds having a structure of $R^A-C(=CR^B_2)COOH$ ($R^A$ and $R^B$ each independently represent a hydrogen atom or a substituent).

The term "acrylamide" refers to all compounds having a structure of $R^C-C(=CR^D_2)CONR^E_2$ ($R^C$, $R^D$, and $R^E$ each independently represent a hydrogen atom or a substituent).

The term "styrene" refers to all compounds having a structure of $R^F-C(=CR^G_2)C_6R^H_6$ ($R^F$, $R^G$, and $R^H$ each independently represent a hydrogen atom or a substituent).

In this specification, when the number of carbon atoms of a certain group is specified, the number of carbon atoms means the number of carbon atoms of the entire group. That is, in the case where the group further has a substituent, the number of carbon atoms means the total number of carbon atoms of the group including the substituent.

In this specification, the weight-average molecular weight (Mw) and the number-average molecular weight (Mn) can be measured as molecular weights in terms of polystyrene by gel permeation chromatography (GPC) unless otherwise specified. At this time, the GPC instrument is HLC-8220 (manufactured by Tosoh Corporation), the column is G3000HXL+G2000HXL (both are TSK-gel HXL (trade name) series manufactured by Tosoh Corporation), the flow rate is 1 mL/min at 23° C., and detection is performed by using refractive index (RI). The eluant can be selected from THF (tetrahydrofuran), chloroform, NMP (N-methyl-2-pyrrolidone), and m-cresol/chloroform (manufactured by Shonan Wako Pure Chemical Industries, Ltd.), and THF is used as long as the target material is dissolved in THF.

In the measurement of the molecular weight of a polymer used in a hydrophilic coating layer, N-methyl-2-pyrrolidone (manufactured by Wako Pure Chemical Industries, Ltd.) is used as an eluant, and TSK-gel Super AWM-H (trade name) manufactured by Tosoh Corporation is used as a column.

The medical lubricating member or the medical device according to an embodiment of the present invention includes a layer disposed on a substrate and having a uniform thickness, is excellent in terms of slidability in a wet state, is excellent in terms of bending resistance, heat resistance, and chemical resistance, and is excellent in terms of adhesiveness between a surface member and the substrate. The composition for a laminated material and the laminated material according to an embodiment of the present invention can provide a medical lubricating member according to an embodiment of the present invention. According to the method for producing a laminated material used for a medical lubricating member according to an embodiment of the present invention, the laminated material can be obtained. According to the method for producing a medical lubricating member according to an embodiment of the present invention, the medical lubricating member can be obtained.

DESCRIPTION OF THE PREFERRED EMBODIMENTS

Figure 1:
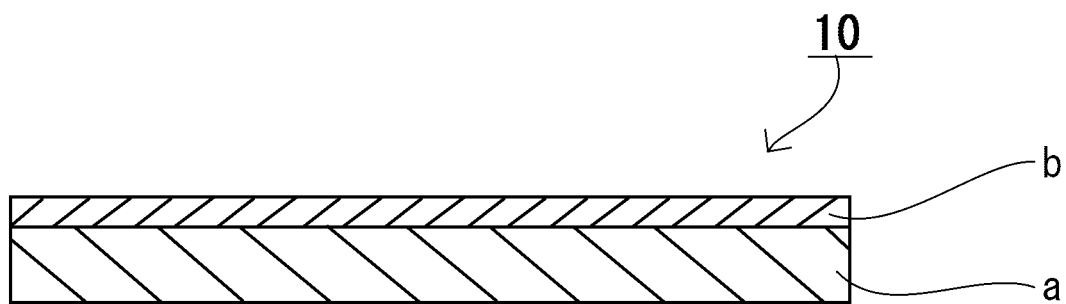
FIG. 1 is a longitudinal sectional view illustrating a laminated material used for a medical lubricating member according to an embodiment of the present invention.

The composition for laminated materials used for the medical lubricating member according to an embodiment of the present invention (hereafter also referred to as a "composition according to an embodiment of the present invention") includes a polymer including a polysiloxane structure, a catalyst for crosslinking reaction, and a crosslinking agent, and can be suitably used for producing a laminated material used for the medical lubricating member according to an embodiment of the present invention (hereafter also referred to as a "laminated material according to an embodiment of the present invention"). Composition according to embodiment of the present invention The composition according to an embodiment of the present invention includes a polymer including a polysiloxane structure, a catalyst for crosslinking reaction, and a crosslinking agent. Hereafter, the polymer including a polysiloxane structure contained in the composition according to an embodiment of the present invention is also referred to as a "polymer b". For the polymer including a polysiloxane structure, the catalyst for crosslinking reaction, and the crosslinking agent, a polymer including a polysiloxane structure, a catalyst for crosslinking reaction, and a crosslinking agent in a laminated material according to an embodiment of the present invention described later can be preferably used.

The polymer b includes at least one of an acrylic acid component, an acrylic acid ester component, an acrylamide component, or a styrene component as a constituent component, and has at least one of a hydroxy group, a carboxy group, an amino group, an isocyanate group, an oxazolinyl group, an epoxy group, a vinyl group, an ethynyl group, a sulfanyl group, an azide group, a trialkoxysilyl group, or an acid anhydride structure.

The crosslinking agent includes at least one of a crosslinking agent having a structural unit represented by formula (CL1) below or a crosslinking agent represented by formula (CL2) below.

Formula (CL1)

Formula (CL2)

In the formulae, $R^{CL}$ represents a hydrogen atom or an organic group. X represents a hydroxy group, a carboxy group, an amino group, an isocyanate group, an oxazolinyl group, an epoxy group, a vinyl group, an ethynyl group, a sulfanyl group, an azide group, a trialkoxysilyl group, or a group having an acid anhydride structure.

Y represents an m-valent linking group, and m represents an integer of 2 or more. $R^{dm}$ has the same definition as X.

The polymer b can be synthesized through the same polymerization reaction of a polymer described in a synthesis method of a crosslinked polymer below.

The weight-average molecular weight of the polymer b is preferably 10,000 to 300,000, more preferably 20,000 to 150,000, and further preferably 20,000 to 120,000.

The composition according to an embodiment of the present invention may include a solvent.

Examples of the solvent that can be included in the composition according to an embodiment of the present invention include ether solvents such as dibutyl ether, dimethoxymethane, dimethoxyethane, diethoxyethane, propylene oxide, 1,4-dioxane, 1,3-dioxolane, 1,3,5-trioxane, tetrahydrofuran, anisole, and phenetole; ketone solvents such as acetone, methyl ethyl ketone, diethyl ketone, dipropyl ketone, diisobutyl ketone, methyl isobutyl ketone, cyclopentanone, cyclohexanone, methylcyclohexanone, and dimethylcyclohexanone; ester solvents such as ethyl formate, propyl formate, n-pentyl formate, methyl acetate, ethyl acetate, methyl propionate, ethyl propionate, n-pentyl acetate, and γ-butyrolactone; alcohol solvents such as methanol, ethanol, 1-propanol, 2-propanol (isopropyl alcohol), 1-butanol, 2-butanol, tert-butanol, 1-pentanol, 2-methyl-2-butanol, and cyclohexanol; aromatic hydrocarbon solvents such as xylene and toluene; halogenated hydrocarbon solvents such as methylene chloride, chloroform, and 1,1-dichloroethane; amide-based solvents such as N-methyl-2-pyrrolidone (NMP), N,N-dimethylformamide (DMF), and N,N-dimethylacetamide (DMAc); nitrile solvents such as acetonitrile; and organic solvents having two or more functional groups, such as methyl 2-methoxyacetate, methyl 2-ethoxyacetate, ethyl 2-ethoxyacetate, ethyl 2-ethoxypropionate, 2-methoxyethanol, 2-propoxyethanol, 2-butoxyethanol, 1,2-diacetoxyacetone, acetylacetone, diacetone alcohol, methyl acetoacetate, N-methylpyrrolidone, propylene glycol monomethyl ether acetate, and ethyl acetoacetate.

When the composition according to an embodiment of the present invention includes a solvent, the content of the solvent in the composition is preferably 40 to 99 mass %, more preferably 50 to 97 mass %, and further preferably 60 to 95 mass %.

The solid content (content ratio) of components other than the solvent included in the composition according to an embodiment of the present invention is as described in the laminated material according to an embodiment of the present invention. The solid content of components other than the solvent refers to a content of components other than a solvent remaining in a laminated material when the laminated material according to an embodiment of the present invention is provided.

The composition according to an embodiment of the present invention is preferably stored at 20° C. to 40° C. with light shielding as necessary in order to suppress the progress of a crosslinking reaction until use. The composition according to an embodiment of the present invention may be prepared by adding a catalyst for crosslinking reaction at the time of use without including the catalyst in advance.

Hereafter, preferred embodiments of the laminated material according to an embodiment of the present invention will be described.

Laminated Material According to Embodiment of the Present Invention

The laminated material according to an embodiment of the present invention is a material for forming a medical lubricating member according to an embodiment of the present invention described later. The laminated material according to an embodiment of the present invention is a laminated body having a substrate (hereafter also referred to as a "substrate a") and a layer (hereafter also referred to as a "layer b") disposed on the substrate a and including a catalyst for crosslinking reaction and a crosslinked polymer including, as a constituent component, a polymer b including a polysiloxane structure described later. The shape of the laminated body is not particularly limited. The laminated material may have a flat surface as illustrated in FIG. 1 or may have a curved surface. The laminated material preferably has, for example, a tubular shape, and may have a spherical shape. The layer b is preferably disposed directly on the substrate a.

Substrate a

The material for the substrate a constituting the laminated material according to an embodiment of the present invention is not particularly limited. Materials that can be used for medical devices and the like can be widely employed. For example, glass, plastic, metal, ceramic, fiber, fabric, paper, leather, synthetic resin, and combinations thereof can be used in accordance with the purpose. In particular, the substrate a is preferably formed of a resin. The shape of the substrate a is not particularly limited, and the substrate a may have, for example, a plate-like shape or a curved surface. The substrate a preferably has a tubular shape and may have a spherical shape.

The substrate a can be suitably used in the present invention even if a surface on which the layer b is to be formed has a low surface free energy. For example, the surface free energy of the surface of the substrate a on which the layer b is to be formed can be set in the range of 5 to 1500 mN/m and can also be set in the range of 10 to 500 mN/m. The surface free energy of the surface of the substrate a on which the layer b is to be formed may be 5 to 300 mN/m, 10 to 200 mN/m, or 10 to 100 mN/m and is also preferably 10 to 50 mN/m. Even when the surface free energy of the surface of the substrate a on which the layer b is to be formed is low, the layer b can be formed on the substrate a without causing cissing or unevenness because the layer b includes a particular crosslinked polymer described later.

The surface free energy can be measured by a typical method. That is, the contact angle of a film is measured with both water and diiodomethane, and is substituted into the following Owens formula (the following is a formula in the case where diiodomethane ($CH_2I_2$) is used as an organic solvent).

Owens Formula $$1+\cos\theta_{H2O}=2(\gamma s^d)^{1/2}(\gamma_{H2O}{}^d)^{1/2}/\gamma_{H2O,V}+2(\gamma s^h)^{1/2}(\gamma_{H2O}{}^h)^{1/2}/\gamma_{H2O,V}$$

$$1+\cos\theta_{CH2I2}=2(\gamma s^d)^{1/2}(\gamma_{CH2I2}{}^d)^{1/2}/\gamma_{CH2I2,V}+2(s^h)^{1/2}(\gamma_{CH2I2}{}^h)^{1/2}/\gamma_{CH2I2,V}$$

Herein, $\gamma_{H2O}{}^d$=21.8, $\gamma_{CH2I2}{}^d$=49.5, $\gamma_{H2O}{}^h$=51.0, $\gamma_{CH2I2}{}^h$=1.3, $\gamma_{H2O,V}$=72.8, and $\gamma_{CH2I2,V}$=50.8. When the measured contact angle of water is substituted into $\theta_{H2O}$ and the measured contact angle of diiodomethane is substituted into $\theta_{CH2I2}$, the dispersion force component $\gamma s^d$ and the polar component $\gamma s^h$ of the surface energy are determined, respectively. The sum $\gamma s^{Vh}=\gamma s^d+\gamma s^h$ can be determined as a surface free energy (mN/m).

The contact angle is measured by setting the droplet volume to 1 μL for both pure water and diiodomethane and reading the contact angle ten seconds after the dropping. At this time, the measurement atmosphere is set to a temperature of 23° C. and a relative humidity of 50%.

The material for the substrate a is, for example, suitably at least one of a urethane resin, a silicone resin, a fluorocarbon resin, an olefin resin, or an acrylic resin. From the viewpoint of use as a medical material, a silicone resin is preferably used. From the viewpoint of further improving layer uniformity and heat resistance, a urethane resin is also preferably used.

Urethane Resin

The urethane resin that can be used as a material for the substrate a is not particularly limited. In general, urethane resins are synthesized by addition polymerization of polyisocyanate and polyol. Examples of the urethane resins that can be used include aliphatic polyurethanes obtained by using an aliphatic isocyanate as a polyisocyanate raw material, aromatic polyurethanes obtained by using an aromatic isocyanate as a polyisocyanate raw material, and copolymers of such polyurethanes.

Furthermore, Pandex series (trade name, manufactured by DIC Corporation), V-Gran series, V-Top series, and DNT-urethane Smile Clean series (trade name, all manufactured by Dai Nippon Toryo Co., Ltd.) serving as urethane resin paints, Polyflex series (trade name, manufactured by DKS Co., Ltd.), Ti-Prene series (trade name, manufactured by Tigers Polymer Corporation), Tecoflex (registered trademark) series (Thermedics Inc.), Miractran series (trade name, manufactured by Nippon Miractran Company Limited), Pellethane series (trade name, manufactured by The Dow Chemical Company), and the like can also be used as the urethane resin.

Silicone Resin

The silicone resin that can be used as a material for the substrate a is not particularly limited, and the silicone resin may be cured using a curing agent. The curing reaction may be a typical reaction. For example, an organohydrogenpolysiloxane and an organopolysiloxane having an ethylenic C=C double bond can be cured using a platinum catalyst. In the case of curing the silicone resin by peroxide crosslinking, a peroxide is used.

Furthermore, rubber compound KE series (trade name, manufactured by Shin-Etsu Chemical Co., Ltd.), ELASTOSIL (registered trademark) series (manufactured by Wacker Asahikasei Silicone Co., Ltd.), SILASTIC (registered trademark) series (manufactured by Dow Corning Toray Co., Ltd.), TSE series (trade name, manufactured by Momentive Performance Materials Japan Co., Ltd.), and the like can be used as the silicone resin.

Fluorocarbon Resin

The fluorocarbon resin that can be used as a material for the substrate a is not particularly limited. For example, polytetrafluoroethylene, polyvinyl fluoride, polyvinylidene fluoride, polytrifluoroethylene, and copolymers thereof can be used.

Furthermore, Teflon (registered trademark, manufactured by DUPONT), Polyflon and Neoflon series (trade name, manufactured by Daikin Industries, Ltd.), Fluon (registered trademark) series and Cytop (registered trademark) series (manufactured by AGC Inc.), Dyneon series (trade name, manufactured by 3M), and the like can also be used as the fluorocarbon resin.

Olefin Resin

The olefin resin that can be used as a material for the substrate a is not particularly limited. For example, polyethylene, polypropylene, polybutene, polypentene, polycyclopentene, polymethylpentene, polystyrene, polybutadiene, polyisoprene, copolymers thereof, and natural rubber can be used. Furthermore, ARTON (registered trademark) series (manufactured by JSR Corporation), SURFLEN (registered trademark) series (manufactured by Mitsubishi Chemical Corporation), ZEONOR (registered trademark) series, ZEONEX (registered trademark) (each manufactured by Zeon Corporation), and the like can also be used as the olefin resin.

Acrylic Resin

The acrylic resin that can be used as a material for the substrate a is not particularly limited. Examples of the acrylic resin include homopolymers such as polymethyl methacrylate, polymethacrylic acid, polymethyl acrylate, polyacrylic acid, polyethyl methacrylate, and polyethyl acrylate and copolymers of the foregoing.

Acrylite Series, Acrypet Series, Acryplen Series (trade name, all manufactured by Mitsubishi Rayon Co., Ltd.), solvent-based acrylic resin for coating Acrydic Series (trade name, manufactured by DIC Corporation), Almatex (registered trademark, manufactured by Mitsui Chemicals, Inc.), Hitaloid (trade name, manufactured by Hitachi Chemical Company, Ltd.), and the like can also be used as the acrylic resin.

Layer b

In the laminated material according to an embodiment of the present invention, the layer b includes a catalyst for crosslinking reaction and a crosslinked polymer (hereafter also referred to as a "crosslinked polymer") including, as a constituent component, a polymer b (hereafter also referred to as a "polymer b") including a polysiloxane structure. When the crosslinked polymer has both a polysiloxane structure and a relatively hydrophilic structure, the affinity of the crosslinked polymer for the surface of the substrate a can be increased even when the surface free energy of the substrate a is low. As a result, a layer including a crosslinked polymer can be formed on the substrate a without causing cissing or unevenness. When the crosslinked polymer has the above-described structure, a layer c described later and disposed on the laminated material according to an embodiment of the present invention has high adhesiveness to the layer b. This makes the thickness of layers disposed on the substrate uniform, which can achieve excellent bending resistance. Furthermore, when the layer b includes a catalyst for crosslinking reaction in the laminated material according to an embodiment of the present invention, the crosslinking density of the crosslinked polymer constituting the layer b is further increased in the layer b, which can provide a stronger laminated material with higher adhesiveness. As a result, heat resistance and chemical resistance can be improved in addition to the above effects.

The polymer b includes, as a constituent component, at least one of an acrylic acid component, an acrylic acid ester component, an acrylamide component, or a styrene component in addition to the component having a polysiloxane structure.

The polymer b has at least one of a hydroxy group, a carboxy group, an amino group, an isocyanate group, an oxazolinyl group (oxazolyl group), an epoxy group, a vinyl group, an ethynyl group, a sulfanyl group, an azide group, a trialkoxysilyl group, or an acid anhydride structure (hereafter, these groups and structures are also collectively referred to as a "reactive functional group" or simply a "reactive group"). These reactive functional groups can interact with or react with a hydrophilic polymer to be applied onto the layer b and described later to further enhance the adhesiveness (adhesive force) between the layer b and the hydrophilic polymer.

The reactive functional group included in the polymer b is preferably at least one of a hydroxy group, a carboxy group, an amino group, an isocyanate group, or a trialkoxysilyl group.

The reactive functional group is preferably included in at least one of the acrylic acid component, the acrylic acid ester component, the acrylamide component, or the styrene component, which are constituent components of the polymer b.

The number of reactive functional groups in one molecule of the polymer b is not particularly limited as long as the effects of the present invention are not impaired. The number is normally 2 or more, preferably 2 to 300, and more preferably 50 to 300.

When the polymer b has a polysiloxane structure in its main chain, the average number of repetitions of polysiloxane is preferably 3 to 10000, more preferably 135 to 5000, and further preferably 200 to 1000. The average number of repetitions may be 100 or more or may be 120 or more. The content of the polysiloxane structure in the polymer b is preferably 1 to 70 mass %, more preferably 5 to 60 mass %, and further preferably 10 to 50 mass %.

When the polymer b has a polysiloxane structure in its side chain (graft chain), the average number n1 of repetitions in formula (1) below can be preferably applied. In this case, the content of the polysiloxane structure in the polymer b is preferably 1 to 70 mass %, more preferably 5 to 60 mass %, and further preferably 10 to 50 mass %.

The average number of repetitions can be calculated by, for example, NMR measurement or the like.

The content of the polysiloxane structure in the polymer b can be calculated based on the content of Si atoms measured by NMR or the like.

The polymer b is preferably a graft polymer having the polysiloxane structure in a graft chain. The graft polymer is preferably a polymer that has a structural unit represented by formula (1) below and having a polysiloxane structure in a graft chain and that has at least one of a structural unit represented by formula (2) below as an acrylic acid component or an acrylic acid ester component, a structural unit represented by formula (3) below as an acrylamide component, or a structural unit represented by formula (4) below as a styrene component.

Herein, the "graft polymer having a polysiloxane structure in a graft chain" refers to a polymer having a graft chain having a polysiloxane structure as a side chain bonded to a polymer main chain. That is, the graft chain is a chain that does not include atoms constituting the main chain.

Structural Unit Having Polysiloxane Structure in Graft Chain

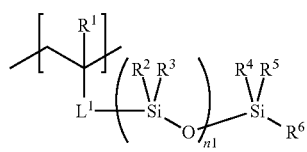

Formula (1)

In the formula (1), $R^1$ to $R^6$ represent a hydrogen atom or an organic group.

Examples of the organic group represented by $R^1$ to $R^6$ include an alkyl group, a cycloalkyl group, an alkenyl group, an aryl group, a heteroaryl group, an alkoxy group, an aryloxy group, a heteroaryloxy group, an alkylthio group, an arylthio group, a heteroarylthio group, an alkylamino group, an arylamino group, a heteroarylamino group, an alkyloxycarbonyl group, an aryloxycarbonyl group, a heteroaryloxycarbonyl group, an alkylaminocarbonyl group, an arylaminocarbonyl group, a heteroarylaminocarbonyl group, and a halogen atom. The organic group is preferably an alkyl group, a cycloalkyl group, an alkenyl group, or an aryl group.

The number of carbon atoms of the alkyl group represented by $R^1$ to $R^6$ is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

The number of carbon atoms of the cycloalkyl group represented by $R^1$ to $R^6$ is preferably 3 to 10, more preferably 5 to 10, and further preferably 5 or 6. The cycloalkyl group is preferably a three-membered ring, a five-membered ring, or a six-membered ring and more preferably a five-membered ring or a six-membered ring. Specific examples of the cycloalkyl group represented by $R^1$ to $R^6$ include cyclopropyl, cyclopentyl, and cyclohexyl.

The number of carbon atoms of the alkenyl group represented by $R^1$ to $R^6$ is preferably 2 to 10, more preferably 2 to 4, and further preferably 2. Specific examples of the alkenyl group include vinyl, allyl, and butenyl.

The number of carbon atoms of the aryl group represented by $R^1$ to $R^6$ is preferably 6 to 12, more preferably 6 to 10, and further preferably 6 to 8. Specific examples of the aryl group include phenyl, tolyl, and naphthyl.

The heteroaryl group represented by $R^1$ to $R^6$ is more preferably a five-membered or six-membered heteroaryl group having at least one of an oxygen atom, a sulfur atom, or a nitrogen atom as a ring-constituting atom. The heteroaryl group may be monocyclic or may have a fused ring. Specific examples of the heteroaryl group include 2-pyridyl, 2-thienyl, 2-furanyl, 3-pyridyl, 4-pyridyl, 2-imidazolyl, 2-benzimidazolyl, 2-thiazolyl, 2-benzothiazolyl, and 2-oxazolyl.

The preferred form of the aryl group constituting the aryloxy group, the arylthio group, the arylamino group, the aryloxycarbonyl group, and the arylaminocarbonyl group that are represented by $R^1$ to $R^6$ is the same as the form of the aryl group represented by $R^1$ to $R^6$.

The preferred form of the heteroaryl group constituting the heteroaryloxy group, the heteroarylthio group, the heteroarylamino group, the heteroaryloxycarbonyl group, and the heteroarylaminocarbonyl group that are represented by $R^1$ to $R^6$ is the same as the form of the heteroaryl group represented by $R^1$ to $R^6$.

The preferred form of the alkyl group constituting the alkoxy group, the alkylthio group, the alkylamino group, the alkyloxycarbonyl group, and the alkylaminocarbonyl group that are represented by $R^1$ to $R^6$ is the same as the form of the alkyl group represented by $R^1$ to $R^6$.

Examples of the halogen atom represented by $R^1$ to $R^6$ include a fluorine atom, a chlorine atom, a bromine atom, and an iodine atom. The halogen atom is preferably a fluorine atom or a bromine atom.

When $R^1$ to $R^6$ represent an organic group, the organic group may be a substituent or may have a substituent.

$R^1$ to $R^6$ preferably represent an alkyl group, a cycloalkyl group, an alkenyl group, or an aryl group, more preferably represent an alkyl group, an alkenyl group, or an aryl group, and further preferably represent an alkyl group having 1 to 4 carbon atoms. Among them, $R^1$ to $R^5$ preferably represent a methyl group, and $R^6$ preferably represents a butyl group.

In the formula (1), $L^1$ represents a single bond or a divalent linking group.

The divalent linking group represented by $L^1$ is not particularly limited as long as the effects of the present invention are produced. When $L^1$ represents a divalent linking group, the molecular weight of $L^1$ is preferably 10 to 200, more preferably 20 to 100, and further preferably 30 to 70.

When $L^1$ represents a divalent linking group, the divalent linking group is preferably, for example, a divalent linking group obtained by combining two or more divalent groups selected from the group consisting of an alkylene group, an arylene group, —C(=O)—, —O—, and —N($R^L$)—. $R^L$ represents a hydrogen atom or a substituent. When $R^L$ represents a substituent, the substituent is preferably an alkyl group. The number of carbon atoms of the alkyl group is preferably 1 to 6 and more preferably 1 to 4, and methyl or ethyl is further preferred.

The alkylene group that may constitute $L^1$ may be linear or branched. The number of carbon atoms of the alkylene group is preferably 1 to 10, more preferably 1 to 6, and further preferably 1 to 3.

The arylene group that may constitute $L^1$ preferably has 6 to 20 carbon atoms and more preferably has 6 to 15 carbon atoms. The arylene group further preferably has 6 to 12 carbon atoms, and is particularly preferably a phenylene group.

$L^1$ preferably represents a divalent linking group obtained by combining two or more divalent groups selected from the group consisting of an alkylene group, —C(=O)—, —O—, and —N($R^L$)—.

The number of combinations of the divalent groups represented by $L^1$ is not particularly limited as long as the molecular weight of $L^1$ is satisfied, and is preferably, for example, 2 to 10.

In the formula (1), n1 represents an average number of repetitions, which is 3 to 10,000. When the structural unit of the formula (1) includes a certain amount of repeating siloxane bonds, the adhesiveness between the substrate a and the layer b can be sufficiently enhanced even if the surface free energy of the surface of the substrate a on which the layer b is to be formed is low. From this viewpoint, n1 is preferably 135 to 10,000, more preferably 150 to 5000, and further preferably 200 to 1000.

The average number of repetitions can be calculated by, for example, NMR measurement.

In the polymer b, the content of the structural unit represented by the formula (1) is preferably 1 to 70 mass %, more preferably 5 to 60 mass %, and further preferably 10 to 50 mass %.

The structural unit represented by the formula (1) can be introduced to the polymer b by using a macromonomer having a particular structure as a raw material. The macromonomer can be synthesized by a typical method, and a commercially available product can also be used. Examples of the commercially available products include X-22-174ASX, X-22-174BX, KF-2012, X-22-2426, and X-22-2404 (trade name, each manufactured by Shin-Etsu Chemical Co., Ltd.), AK-5, AK-30, and AK-32 (trade name, each manufactured by Toagosei Co., Ltd.), and MCR-M07, MCR-MT, MCR-M17, and MCR-M22 (trade name, each manufactured by Gelest, Inc.).

Acrylic Acid Component or Acrylic Acid Ester Component

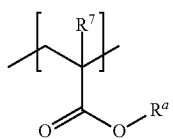

Formula (2)

In formula (2), $R^7$ and $R^a$ represent a hydrogen atom or an organic group.

The form of the organic group represented by $R^7$ may be the form of the organic group represented by $R^1$ in the above formula (1). Among them, $R^7$ preferably represents a hydrogen atom or an alkyl group. The number of carbon atoms of the alkyl group is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

The form of the organic group represented by $R^a$ may be the form of the organic group represented by $R^1$ in the above formula (1). Among them, $R^a$ preferably represents a hydrogen atom, an alkyl group, or an aryl group. The alkyl group represented by $R^a$ preferably has 1 to 10 carbon atoms and more preferably has 1 to 6 carbon atoms. Specific examples of the alkyl group include methyl, ethyl, n-propyl, isopropyl, n-butyl, isobutyl, n-hexyl, n-octyl, 2-ethylhexyl, and n-decyl.

The aryl group represented by $R^a$ preferably has 6 to 12 carbon atoms, more preferably has 6 to 10 carbon atoms, further preferably has 6 to 8 carbon atoms, and particularly preferably has 6 carbon atoms. Specific examples of the aryl group include phenyl, tolyl, and naphthyl.

When $R^7$ and $R^a$ represent an organic group, the organic group may be unsubstituted or substituted. When the polymer b has the structural unit represented by the formula (2), at least a part of the structural units represented by the formula (2) in the polymer b preferably has the above-described reactive functional group as a substituent.

In the structural unit represented by the formula (2) in the polymer b, when $R^a$ represents an alkyl group having a substituent, $R^a$ also preferably represents a group represented by formula (5) below in at least a part of the structural units.

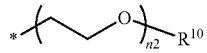

Formula (5)

In the formula (5), n2 represents an average number of repetitions, which is 1 to 10,000. Herein, n2 preferably represents 1 to 8000, more preferably represents 1 to 5000, and further preferably represents 1 to 3000.

The average number of repetitions can be calculated by, for example, NMR measurement.

$R^{10}$ represents a hydrogen atom or an organic group. The form of the organic group represented by $R^1$ may be the form of the organic group represented by $R^1$ in the above formula (1). When $R^{10}$ represents an organic group, the organic group may be unsubstituted or substituted. $R^{10}$ preferably represents a hydrogen atom or an alkyl group. Specific examples of the alkyl group include methyl, ethyl, n-propyl, isopropyl, n-butyl, isobutyl, n-hexyl, n-octyl, 2-ethylhexyl, and n-decyl.

* represents a bonding site to an oxygen atom (—O—) in the formula (2).

$R^a$ also preferably represents a nitrogen-containing organic group in at least a part of the structural units represented by the formula (2) that may be present in the polymer b. The molecular weight of the nitrogen-containing organic group is preferably 10 to 200 and more preferably 20 to 100. The nitrogen-containing organic group is preferably an amino group (including a substituted amino group in addition to an unsubstituted amino group). Preferred examples of the nitrogen-containing organic group include an alkylamino group, an alkylaminoalkyl group, an arylamino group, an arylaminoalkyl group, a heteroarylamino group, and a heteroarylaminoalkyl group.

When $R^a$ represents the group represented by the formula (5) or the nitrogen-containing organic group, it is believed that the interaction between the polymer b including a polysiloxane structure and a crosslinking agent component is strengthened.

Acrylamide Component

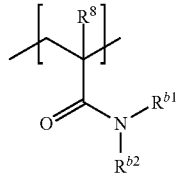

Formula (3)

In the formula (3), $R^8$, $R^{b1}$, and $R^{b2}$ represent a hydrogen atom or an organic group. The form of the organic group represented by $R^8$ may be the form of the organic group represented by $R^1$ in the above formula (1). $R^8$ preferably represents a hydrogen atom or an alkyl group and more preferably represents an alkyl group. The number of carbon atoms of the alkyl group is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

The organic group represented by $R^{b1}$ and $R^{b2}$ is, for example, the organic group represented by $R^1$ in the above formula (1). In particular, $R^{b1}$ and $R^{b2}$ preferably represent a hydrogen atom, an alkyl group, or an aryl group. The number of carbon atoms of the aryl group is preferably 6 to 12, more preferably 6 to 10, further preferably 6 to 8, and particularly preferably 6. Specific examples of the aryl group include phenyl, tolyl, and naphthyl.

When $R^8$, $R^{b1}$, and $R^{b2}$ represent an organic group, the organic group may be unsubstituted or substituted. When the polymer b has the structural unit represented by the formula (3), at least a part of the structural units represented by the formula (3) in the polymer b preferably has the above-described reactive functional group as a substituent.

Styrene Component

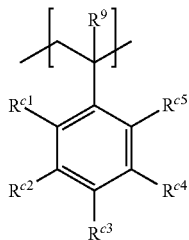

Formula (4)

In Formula (4), $R^9$ represents a hydrogen atom or an organic group. $R^{c1}$ to $R^{c5}$ represent a hydrogen atom, a halogen atom, or an organic group.

The form of the organic group represented by $R^9$ may be the form of the organic group represented by $R^1$ in the above formula (1). In particular, $R^9$ preferably represents a hydrogen atom.

The form of the organic group represented by $R^{c1}$ to $R^{c5}$ may be the form of the organic group represented by $R^1$ in the above formula (1). The halogen atom represented by $R^{c1}$ to $R^{c5}$ is not particularly limited. The halogen atom is preferably a fluorine atom or a bromine atom and more preferably a fluorine atom. $R^{c1}$ to $R^{c5}$ preferably represent a hydrogen atom, an alkyl group, or a halogen atom. The number of carbon atoms of the alkyl group is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

When $R^9$ and $R^{c1}$ to $R^{c5}$ represent an organic group, the organic group may be unsubstituted or substituted. When the polymer b has the structural unit represented by the formula (4), at least a part of the structural units represented by the formula (4) in the polymer b preferably has the above-described reactive functional group as a substituent.

When the polymer b has a structural unit represented by any of the formulae (2) to (4), the total amount of the structural unit in the polymer b is preferably 10 to 90 mass %, more preferably 15 to 80 mass %, and further preferably 20 to 70 mass %.

When the polymer b has a structural unit that is represented by any of the formulae (2) to (4) and that has the above-described reactive functional group, the content of the structural unit in the polymer b is preferably 5 to 70 mass %, more preferably 10 to 50 mass %, further preferably 10 to 30 mass %, and particularly preferably 15 to 30 mass %. In this case, a structural unit other than the structural unit that is represented by any of the formulae (2) to (4) and that has the above-described reactive functional group of the polymer b is preferably used in combination.

The polymer b may have a structural unit other than the structural unit represented by the formula (1) and the structural unit represented by any of the formulae (2) to (4) as long as the effects of the present invention are produced.

The crosslinked polymer has a crosslinked structure constituted by a crosslinking agent component (hereafter, the crosslinked structure constituted by a crosslinking agent component is also referred to as a "particular crosslinked structure"). In this case, the crosslinking agent component includes at least one of a crosslinking agent (polymeric crosslinking agent) having a structural unit represented by formula (CL1) below or a crosslinking agent represented by formula (CL2) below. By forming a crosslinked structure using these crosslinking agents, the layer b can be cured to further increase the mechanical strength. In these crosslinking agents, the reactive functional group of each of the above-described structural units and the reactive group of the crosslinking agent (preferably, X in the formula (CL1) or $R^{dm}$ in the formula (CL2)) normally interact or react with each other to form a crosslinked structure in the crosslinked polymer. The crosslinking reaction can be caused by a typical method in accordance with the type of group contributing to the crosslinking reaction.

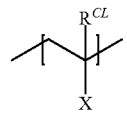

Formula (CL1)

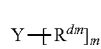

Formula (CL2)

In the formula (CL1), $R^{CL}$ represents a hydrogen atom or an organic group. When $R^{CL}$ represents an organic group, the organic group may have a substituent. $R^{CL}$ preferably represents a hydrogen atom or an alkyl group (preferably an alkyl group having 1 to 5 carbon atoms, more preferably an alkyl group having 1 to 3 carbon atoms). X represents a hydroxy group, a carboxy group, an amino group, an isocyanate group, an oxazolinyl group, an epoxy group, a vinyl group, an ethynyl group, a sulfanyl group, an azide group, a trialkoxysilyl group, or a group having an acid anhydride structure. X may have a substituent.

The crosslinking agent represented by the formula (CL1) is, for example, an oxazoline ring-containing polymer (trade name: EPOCROS (registered trademark), manufactured by Nippon Shokubai Co., Ltd.). The oxazoline ring-containing polymer is, for example, a polymer constituted by the following structural units. In this specification, Me represents methyl.

When the crosslinking agent is a polymer and includes an acrylic acid component, an acrylic acid ester component, an acrylamide component, or a styrene component as a constituent component, the description of the acrylic acid component, the acrylic acid ester component, the acrylamide component, and the styrene component as the constituent components of the polymer b can be preferably applied to these components. Examples of the crosslinking agent represented by the formula (CL1) are shown below.

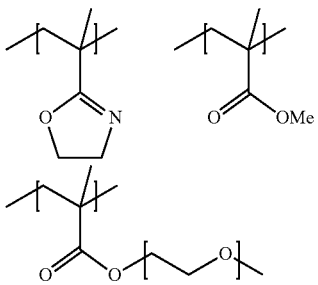

In the formula (CL2), Y represents an m-valent linking group. Y preferably represents a hydrocarbon group having 2 to 20 carbon atoms and more preferably represents a hydrocarbon group having 2 to 15 carbon atoms. These hydrocarbon groups may have a heteroatom in their hydrocarbon chain. Examples of the hetero atom include O, S, N, and Ti. Furthermore, m represents an integer of 2 or more, preferably represents an integer of 2 to 8, and more preferably represents an integer of 2 to 4. $R^{dm}$ has the same definition as X in the formula (CL1).

Examples of the crosslinking agent represented by the formula (CL2) include polyisocyanate compounds (preferably diisocyanate compounds), silane coupling agents, and titanium coupling agents. Examples of the crosslinking agent represented by the formula (CL2) are shown below.

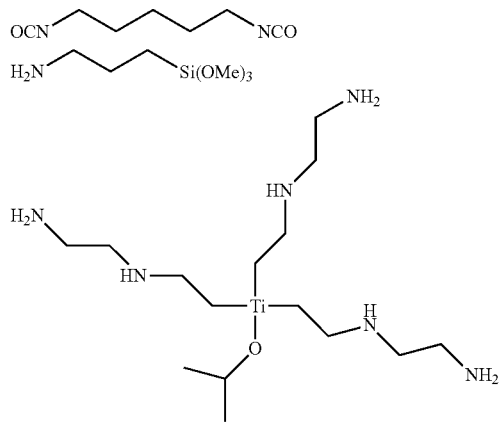

In the crosslinked polymer, the content of the crosslinking agent component (crosslinking agent-derived component) is preferably 30 to 90 mass %, more preferably 30 to 80 mass %, and further preferably 40 to 70 mass %.

The crosslinked polymer can be synthesized by a typical method so as to be contained in the layer b. For example, a polymer (preferably polymer b) is obtained by polymerizing a monomer that results in a desired structural unit other than a crosslinking agent component by a typical method using a polymerization initiator. The polymer is crosslinked using a crosslinking agent in the presence of a catalyst for cross-linking reaction to obtain a crosslinked polymer. The polymerization reaction may be any of anionic polymerization, cationic polymerization, and radical polymerization, but radical polymerization is preferred.

Any polymerization initiator can be used in accordance with the form of the polymerization reaction (anionic polymerization, cationic polymerization, or radical polymerization). The polymerization initiator may be either a thermal polymerization initiator or a photopolymerization initiator. The molecular weight of the polymerization initiator is not limited, and any polymerization initiator having a low molecular weight to a high molecular weight may be used.

Specific examples of the radical polymerization initiator include organic peroxides and azo compounds.

Catalyst for Crosslinking Reaction

The catalyst for crosslinking reaction used in the present invention is not particularly limited as long as it is a catalyst that promotes the reaction of forming the particular crosslinked structure. That is, in this specification, the "catalyst for crosslinking reaction" is a catalyst that promotes (i) formation of a crosslinked structure through a covalent bond between the polymer b and the crosslinking agent and (ii) formation of a crosslinked structure through interaction between the polymer b and the crosslinking agent, for example, intermolecular interaction such as van der Waals force or hydrogen bond.

For the catalyst for crosslinking reaction, for example, a metal or a compound that is normally used as a catalyst for the above reaction can be widely used. Examples of such a catalyst include organic metals, organic acid metal salts, metal hydroxides, acids, bases, metal chelate compounds, and hydrolysates of metal chelate compounds. For example, in a crosslinking reaction using an isocyanate group, an organic metal, an acid, or the like causes a nucleophilic or electrophilic reaction and functions as a catalyst, thereby promoting the desired crosslinking reaction.

These catalysts for crosslinking reaction can be used alone or in combination of two or more.

Examples of the organic metal include alkyl metal compounds such as tetramethyltitanium and tetrapropylzirconium; and metal alcoholates such as metal propoxide, metal isopropoxide, and metal n-butoxide.

Specific examples of the metal alcoholate include tetraisopropoxytitanium and tetrabutoxyzirconium.

The organic acid metal salt is, for example, a compound that is a salt obtained from a metal ion and an organic acid. Examples of the organic acid include carboxylic acids such as 2-ethylhexyl acid, acetic acid, oxalic acid, tartaric acid, and benzoic acid; sulfur-containing organic acids such as organic sulfonic acids and organic sulfinic acids; phenolic compounds; enol compounds; oxime compounds; imide compounds; and organic compounds exhibiting acidity, such as aromatic sulfonamide.

Specific examples of the organic acid metal salt include tin octoate, lead octoate, cobalt octoate, zinc octoate, calcium octoate, zinc naphthenate, cobalt naphthenate, di-n-butyltin diacetate, di-n-butyltin dioctoate, di-n-butyltin dilaurate, and di-n-butyltin maleate.

The metal hydroxide is a metal compound having a hydroxide ion as an anion. Examples of the metal hydroxide include lithium hydroxide, sodium hydroxide, and potassium hydroxide.

The metal chelate compound is a compound in which a ligand is coordinated to a metal or a metal ion. Preferred metals or metal ions are described below.

Ligands are generally compounds having, in its partial structure, a coordinating atom or a group, such as a hydroxy group or an anion thereof or an atom having a lone pair (e.g., an oxygen atom such as —O— or >C(=O), a nitrogen atom such as —$NH_2$ or —NH—, and a sulfur atom such as —SH, —S—, —S—, or >C(=S)). The ligand preferably has two or more of these coordinating atoms or groups in its molecule. In this case, the metal chelate compound is preferably a compound in which a central metal or metal ion and a ligand form a five- or six-membered ring through an ionic bond or a coordinate bond.

Two or more ligands may be coordinated with a metal or a metal ion.

Examples of a monodentate ligand having one coordinating atom include an alkoxy group, an acyloxy group, a halogen group, and an isocyanate group. The monodentate ligand is preferably an alkoxy group having 1 to 4 carbon atoms or an acyloxy group having 1 to 4 carbon atoms.

The bidentate ligand having two coordinating atoms is preferably a β-ketocarbonyl compound, a β-ketoester compound, or an α-hydroxyester compound. Specific examples of the bidentate ligand include β-ketoesters such as methyl acetoacetate, n-propyl acetoacetate, isopropyl acetoacetate, n-butyl acetoacetate, sec-butyl acetoacetate, and tert-butyl acetoacetate; β-diketones such as acetylacetone, hexane-2,4-dione, heptane-2,4-dione, heptane-3,5-dione, octane-2,4-dione, nonane-2,4-dione, and 5-methylhexane-2,4-dione; and α-hydroxycarboxylic acids such as glycolic acid and lactic acid.

In addition to the above ligands, monoalkyl phosphoric acid, dialkyl phosphoric acid, monoalkyl phosphorous acid, and dialkyl phosphorous acid may be used.

For the monoalkyl phosphoric acid, the dialkyl phosphoric acid, the monoalkyl phosphorous acid, and the dialkyl phosphorous acid, the number of carbon atoms of the alkyl group is preferably 1 to 20 and more preferably 4 to 16.

Specific examples of the hydrolysate of the metal chelate compound include silicic acid, titanic acid, zirconic acid, and stannic acid.

Examples of the metal in the organic metal, the organic acid metal salt, the metal hydroxide, and the metal chelate compound include titanium (Ti), zirconium (Zr), aluminum (Al), silicon (Si), germanium (Ge), indium (In), tin (Sn), tantalum (Ta), zinc (Zn), tungsten (W), and lead (Pb). In particular, the metal is preferably titanium (Ti), zirconium (Zr), aluminum (Al), and tin (Sn) and more preferably titanium (Ti). These metals may be used alone or in combination of two or more. Examples of the metal ion include ions of these metals.

The acid may be any of an organic acid and an inorganic acid such as a mineral acid. Examples of the organic acid include carbonic acid in addition to the blocked acid, sulfonic acid, phosphate acid, Lewis acid, and carboxylic acid described later. Examples of the sulfonic acid include polyoxyethylene alkylsulfuric acid and polyoxyethylene alkylarylsulfuric acid, in addition to those described later. Examples of the mineral acid include phosphoric acid, hydrochloric acid, nitric acid, boric acid, and fluoroboric acid.

Examples of the base include strong bases such as tetramethylguanidine and tetramethylguanidylpropyltrimethoxysilane, organic amines, salts obtained by neutralizing an organic amine with carboxylic acid, quaternary ammonium salts, sodium methylate, tetramethylammonium hydroxide, tributylamine, diazabicycloundecene, ethylenediamine, diethylenetriamine, ethanolamine, γ-aminopropyltrimethoxysilane, and γ-(2-aminoethyl)-aminopropyltrimethoxysilane.

In the present invention, an acid catalyst is preferably used as the catalyst for crosslinking reaction in order to improve the chemical resistance of the layer b while enhancing the adhesiveness between the substrate a and the layer b. The acid catalyst may be blocked or unblocked. The acid catalyst is preferably at least one of a blocked acid, sulfonic acid, phosphate acid, Lewis acid, or carboxylic acid described later, and more preferably at least one of sulfonic acid, phosphate acid, or carboxylic acid.

Blocked Acid

By using a blocked acid, the pot life of the composition according to an embodiment of the present invention can be increased. Specific examples of the blocked acid include 2-amino-2-methyl-1-propanol-blocked p-toluenesulfonic acid, triethylamine-blocked p-toluenesulfonic acid, dimethylaminoethanol-blocked p-toluenesulfonic acid, dodecylbenzene sulfonic acid, and ammonium chloride.

The term "blocked acid" refers to "a compound obtained by converting a functional group of an acid into a salt or an ester, and the compound can be returned to the acid again by a trigger such as heating".

Sulfonic Acid

Specific examples of the sulfonic acid include alkylbenzenesulfonic acids (e.g., dodecylbenzenesulfonic acid), alkylsulfonic acids (e.g., methanesulfonic acid), alkylsulfosuccinic acids, polyoxyethylene distyryl phenyl ether sulfonic acid, p-toluenesulfonic acid, p-toluenesulfonic acid monohydrate, dinonylnaphthalenemonosulfonic acid, and dinonylnaphthalenedisulfonic acid.

Phosphate Acid

Specific examples of the phosphate acid include n-butyl acid phosphate and phenyl acid phosphate. Examples of the phosphate acid also include photo-acid generators that generate an acid through irradiation with light, such as diphenyliodonium hexafluorophosphate and triphenylphosphonium hexafluorophosphate.

Lewis Acid

Specific examples of the Lewis acid include magnesium bromide, magnesium nitrate, and zinc oxalate.

Carboxylic Acid

Specific examples of the carboxylic acid include acetic acid, formic acid, oxalic acid, phthalic acid, trifluoroacetic acid, propionic acid, octanoic acid, cyclohexanecarboxylic acid, benzoic acid, toluic acid, phenylacetic acid, p-tert-butylbenzoic acid, and p-methoxyphenylacetic acid.

The catalysts for crosslinking reaction according to an embodiment of the present invention may be used alone or in combination of two or more.

In the laminated material according to an embodiment of the present invention, the content of the catalyst for crosslinking reaction is preferably 0.1 to 20 mass %, more preferably 0.5 to 10 mass %, and further preferably 1.0 to 5.0 mass %.

A polymer b or two or more polymers b may be used to form the crosslinked polymer.

The content of the polymer b in the crosslinked polymer is preferably 10 mass % or more, more preferably 20 mass % or more, and further preferably 30 mass % or more. The upper limit is preferably 90 mass % or less, more preferably 80 mass % or less, and further preferably 70 mass % or less.

The content of the crosslinked polymer in the layer b is preferably 10 mass % or more, more preferably 20 mass % or more, and further preferably 30 mass % or more. The upper limit is preferably 90 mass % or less, more preferably 80 mass % or less, and further preferably 70 mass % or less.

When the layer b includes a component other than the crosslinked polymer, the component other than the crosslinked polymer is, for example, a filler, a film-forming aid, and a viscosity modifier.

Filler

In the present invention, for example, a metal powder can be used as a filler. The metal powder may be a metal powder formed of a single metal atom or an alloy powder formed of a plurality of metal atoms. Examples of the metal element constituting the metal powder include metal atoms such as silicon, aluminum, silver, copper, magnesium, iron, chromium, nickel, titanium, zirconium, zinc, tin, molybdenum, and tungsten. Examples of the filler include oxides of these metals and hydrolytic condensation products of these oxides.

Examples of the filler include silicas such as dry-process silica and wet-process silica; nitrides such as boron nitride, aluminum nitride, and silicon nitride; sulfates such as barium sulfate, calcium sulfate, magnesium sulfate, iron sulfate, and copper sulfate; hydroxides such as aluminum hydroxide, magnesium hydroxide, and calcium hydroxide; silicates such as silicic acid, aluminum silicate, magnesium silicate, and calcium silicate; carbonates such as calcium carbonate, calcium-magnesium carbonate (CaMg(CO$_3$)$_2$), and magnesium carbonate; borates such as aluminum borate, zinc borate, and calcium borate; titanates such as potassium titanate; minerals such as kaolinite, talc, natural mica, and synthetic mica; carbides such as silicon carbide; fine quartz powder; diatomaceous earth powder; and glass fiber.

These fillers may be used without any treatment. They may be surface-treated with a silane coupling agent, an aluminate coupling agent, a titanate coupling agent, a silane, a silazane, a polysiloxane having a low degree of polymerization, or the like in accordance with the required characteristics. Further, a fine-powder inorganic filler obtained by surface-treating these fillers with silicone oil or the like may be used.

These fillers may be used alone or in combination of two or more.

In the present invention, it is preferable to use at least one of silicon, aluminum, titanium, zirconium, zinc, tin, iron, oxides thereof, or hydrolytic condensation products of these oxides in order to suppress deterioration of slidability, adhesiveness, and chemical resistance. It is more preferable to use at least one of silicon, aluminum, oxides thereof, or hydrolytic condensation products of these oxides in order to further improve heat resistance. It is further preferable to use silicon oxide or aluminum oxide.

By using fumed silica, both heat resistance and layer uniformity can also be improved.

Film-Forming Aid

The film-forming aid used in the present invention is not particularly limited, but it is preferable to use an anionic surfactant (e.g., dioctyl sulfosuccinate sodium salt), a nonionic surfactant (e.g., sorbitan monooleate), a polyether-modified siloxane, or a silicone oil in order to suppress deterioration of slidability, adhesiveness, chemical resistance, and heat resistance. It is more preferable to use an anionic surfactant or a nonionic surfactant in order to further improve layer uniformity.

Examples of the anionic surfactant include sulfonate anionic surfactants such as alkylarylsulfonates, alkylsulfonates, and ester sulfonates; phosphate anionic surfactants such as alkylphosphates; sulfate anionic surfactants such as alkylsulfates and alkylether sulfates; and carboxylate anionic surfactants such as alkyl fatty acid salts. Among them, a sulfonate anionic surfactant is preferred from the viewpoint of improving the layer uniformity in a small amount of surfactant added.

Examples of the sulfonate anionic surfactant include alkylarylsulfonates such as butylbenzenesulfonates, hexylbenzenesulfonates, octylbenzenesulfonates, decylbenzenesulfonates, dodecylbenzenesulfonates, tetradecylbenzenesulfonates, hexadecylbenzenesulfonates, octadecylbenzenesulfonates, dibutylnaphthalenesulfonates, and triisopropylnaphthalenesulfonates; alkylsulfonates such as decylsulfonates, dodecylsulfonates, tetradecylsulfonates, hexadecylsulfonates, and octadecylsulfonates; and ester sulfonates such as dibutyl sulfosuccinates, dioctyl sulfosuccinates, dodecyl sulfoacetates, and nonylphenoxypolyethylene glycol sulfoacetates. Among them, the number of carbon atoms of the alkyl group is 8 or more, preferably 10 to 22, and more preferably 12 to 18 from the viewpoint of achieving excellent heat resistance. From the viewpoint of achieving excellent preservation stability of a coating liquid, the number of carbon atoms of the aryl group is preferably 6 to 14 and more preferably 6 to 10. The salt is preferably a metal salt, more preferably an alkali metal salt such as a lithium salt, a sodium salt, or a potassium salt, and further preferably a sodium salt. From the viewpoint of improving the layer uniformity without deteriorating other characteristics, an alkylarylsulfonate or an alkylsulfonate is preferred.

The nonionic surfactant is not particularly limited. Examples of the nonionic surfactant include ether surfactants such as polyoxyethylene nonylphenyl ether, polyoxyethylene octylphenyl ether, polyoxyethylene dodecylphenyl ether, polyoxyethylene oleyl ether, polyoxyethylene lauryl ether, and polyoxyethylene alkyl ethers (the alkyl group has 4 to 20 carbon atoms); and ester surfactants such as polyoxyethylene oleate, polyoxyethylene distearate, sorbitan laurate, sorbitan monostearate, sorbitan monooleate, sorbitan sesquioleate, polyoxyethylene monooleate, and polyoxyethylene stearate.

Examples of the polyether-modified siloxane include alkylsiloxanes modified with polyether. The polyether-modified siloxane is, for example, a polyether-modified polydimethylsiloxane represented by formula below and described in paragraph [0070] of JP2015-142974A.

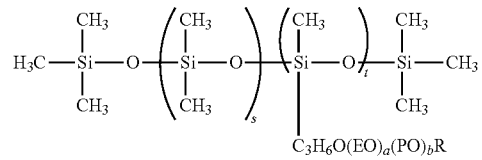

In the formula, R represents a hydrogen atom, a methyl group, a hydroxy group, a carboxy group, or a benzyl group. Herein, s represents an integer of 2 to 27, and t represents an integer of 1 to 15. Furthermore, a represents an integer of 0 to 20, and b represents an integer of 0 to 20.

Note that "EO" refers to "—$C_2H_4O$—" and "PO" refers to "—$C_3H_6O$—".

Commercially available film-forming aids can be used. Examples of the film-forming aid include BYK 349 (silicone oil manufactured by BYK), KF-351A and KF-615 (modified silicone oil manufactured by Shin-Etsu Silicone Co., Ltd.), SANSEPARER 100 (anionic surfactant manufactured by Sanyo Chemical Industries, Ltd.), Rheodol AO-10V (nonionic surfactant manufactured by Kao Corporation), KF-6013 (polyether-modified siloxane manufactured by Shin-Etsu Chemical Co., Ltd.), and KF-54 (silicone oil manufactured by Shin-Etsu Chemical Co., Ltd.) (all trade name).

The film-forming aids may be used alone or in combination of two or more.

Viscosity Modifier

The viscosity modifier can be used to adjust the viscosity and thixotropy of the composition according to an embodiment of the present invention to a desired level. The viscosity of the composition according to an embodiment of the present invention is desirably set such that the layer b can be formed on the substrate a at a desired thickness. The viscosity of the composition according to an embodiment of the present invention can be adjusted to 50 cps to 500 cps, but a higher or lower viscosity is desirable in some cases. Examples of the viscosity modifier include cellulose-based viscosity modifiers such as carboxymethyl cellulose, methyl cellulose, hydroxyethyl cellulose, and cellulose acetate butyrate; polycarboxylic acid-based viscosity modifiers such as sodium polyacrylate, alkali-soluble emulsions, and alkali-soluble associative emulsions; polyethylene glycol-based viscosity modifiers such as polyethylene glycol, polyethylene glycol alkyl ethers, polyethylene glycol alkyl esters, and associative polyethylene glycol derivatives; other water-soluble polymer-based viscosity modifiers such as polyvinyl alcohol; smectite-based viscosity modifiers such as montmorillonite, hectorite, and saponite; and acrylate polymers such as ethyl acrylate/2-ethylhexyl acrylate copolymer. The number of carbon atoms of the polyethylene glycol alkyl ether and the polyethylene glycol alkyl ester is preferably 1 to 25 and more preferably 4 to 20.

The viscosity modifiers may be used alone or in combination of two or more.

In the present invention, at least one of ethyl acrylate/2-ethylhexyl acrylate copolymer or cellulose acetate butyrate is preferably used because they are excellent in terms of compatibility with the polymer b and the crosslinking agent, can suppress the occurrence of haze, and suppress deterioration of the mechanical strength of layers.

The filler, the film-forming aid, and the viscosity modifier may be used alone or in combination of two or more. In the laminated material according to an embodiment of the present invention, the filler, the film-forming aid, and the viscosity modifier may be constituent components of the crosslinked polymer through at least one of an interaction or a covalent bond.

In the laminated material according to an embodiment of the present invention, the total content of the filler, the film-forming aid, and the viscosity modifier is preferably 0.1 to 50 mass %, more preferably 1 to 30 mass %, and further preferably 3 to 20 mass %.

However, in the case where the filler, the film-forming aid, and the viscosity modifier are constituent components of the crosslinked polymer through a covalent bond, the above-content is an amount of materials added when a composition for forming the laminated material according to an embodiment of the present invention (e.g., the composition according to an embodiment of the present invention) is prepared.

The surface of the layer b is preferably subjected to hydrophilic treatment. In the present invention, the "surface of the layer b" means a surface opposite to a surface of the layer b in contact with the substrate a.

The method of hydrophilic treatment is not particularly limited as long as a hydrophilic group can be provided to the surface of the layer b (a crosslinked polymer present on the surface of the layer b). For example, the surface of the layer b can be hydrophilized by immersion in an acidic solution, immersion in an alkaline solution, immersion in a peroxide solution, plasma treatment, or electron beam irradiation.

The thickness of the layer b is normally 0.01 to 100 μm, preferably 0.05 to 50 μm, and more preferably 0.1 to 10 μm.

Method for Producing Laminated Material According to Embodiment of the Present Invention The method for producing a laminated material according to an embodiment of the present invention is a method for producing a laminated material used for a medical lubricating member and having a substrate a and a layer b disposed on the substrate a. The method includes a step of forming the layer b by applying a composition including the polymer b, the catalyst for crosslinking reaction, and the crosslinking agent onto the substrate a.

The coating method is not particularly limited. Examples of the method include a coating method in which the substrate a is immersed in the composition, a coating method in which the composition is applied onto the substrate a with a blade coater, a die coater, or a bar coater, a coating method in which the composition is sprayed onto the substrate a, a coating method in which spin-coating is performed on the substrate a using a spinner, an inkjet coating method, and a coating method that uses screen printing, gravure printing, or flexographic printing.

The method for producing a laminated material according to an embodiment of the present invention may include a heating step. The heating conditions are, for example, 40° C. to 250° C. and 1 to 120 minutes.

The method for producing a laminated material according to an embodiment of the present invention may include a hydrophilic treatment. The hydrophilic treatment includes immersion in a 10% aqueous hydrochloric acid solution, a 5% aqueous sodium hydroxide solution, acetic acid, or a hydrogen peroxide solution for 30 to 640 minutes, followed by washing with methanol, ethanol, propanol, or isopropanol and drying at 40° C. to 100° C. for 10 to 90 minutes.

Medical Lubricating Member

Figure 2:
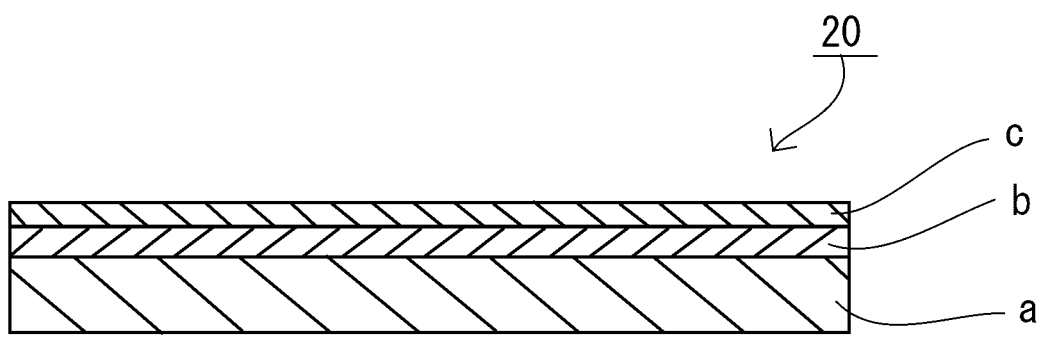
FIG. 2 is a longitudinal sectional view illustrating a medical lubricating member according to an embodiment of the present invention.

The medical lubricating member according to an embodiment of the present invention is provided by forming a layer c including a hydrophilic polymer on the surface of the layer b constituting the laminated material according to an embodiment of the present invention. That is, as illustrated in FIG. 2 (FIG. 2 illustrates one embodiment in which a medical lubricating member is produced using the laminated material in FIG. 1), the medical lubricating member according to an embodiment of the present invention has the laminated material according to an embodiment of the present invention and a layer c including a hydrophilic polymer and disposed on the layer b (the surface of the layer b) constituting the laminated material. Examples of the hydrophilic polymer include polyvinylpyrrolidone, a vinyl ether-maleic anhydride copolymer, polyethylene glycol, polyacrylic acid, polyacrylamide, and hyaluronic acid. One or more of the hydrophilic polymers can be used. The hydrophilic polymer is preferably at least one of polyvinylpyrrolidone, a maleic anhydride-vinyl ether copolymer, or polyethylene glycol, and more preferably polyvinylpyrrolidone or a maleic anhydride-vinyl ether copolymer from the viewpoint of further improving layer uniformity, heat resistance, and bending resistance.

The content of the hydrophilic polymer in the layer c is preferably 50 mass % or more, more preferably 70 mass % or more, further preferably 80 mass % or more, and particularly preferably 90 mass % or more. When the layer c includes a component other than the hydrophilic polymer, examples of the component other than the hydrophilic polymer include a polymer binder, a surfactant, polymer fine particles, inorganic fine particles, and a crosslinking agent.

The layer c can be formed by preparing a solution (a coating solution for forming a layer c) in which a hydrophilic polymer is dissolved, applying this solution onto the layer b, and drying the solution. The solution may contain a crosslinking agent in accordance with the purpose. Examples of the solvent used for the coating solution for forming a layer c include ether solvents such as dibutyl ether, dimethoxymethane, dimethoxyethane, diethoxyethane, propylene oxide, 1,4-dioxane, 1,3-dioxolane, 1,3,5-trioxane, tetrahydrofuran, anisole, and phenetole; ketone solvents such as acetone, methyl ethyl ketone, diethyl ketone, dipropyl ketone, diisobutyl ketone, methyl isobutyl ketone, cyclopentanone, cyclohexanone, methylcyclohexanone, and dimethylcyclohexanone; ester solvents such as ethyl formate, propyl formate, n-pentyl formate, methyl acetate, ethyl acetate, methyl propionate, ethyl propionate, n-pentyl acetate, and γ-butyrolactone; alcohol solvents such as methanol, ethanol, 1-propanol, 2-propanol, 1-butanol, 2-butanol, tert-butanol, 1-pentanol, 2-methyl-2-butanol, and cyclohexanol; aromatic hydrocarbons such as xylene and toluene; halogenated hydrocarbon solvents such as methylene chloride, chloroform, and 1,1-dichloroethane; amide solvents such as N-methyl-2-pyrrolidone (NMP), N,N-dimethylformamide (DMF), and N,N-dimethylacetamide (DMAc); nitrile solvents such as acetonitrile; and organic solvents having two or more functional groups, such as methyl 2-methoxyacetate, methyl 2-ethoxyacetate, ethyl 2-ethoxyacetate, ethyl 2-ethoxypropionate, 2-methoxyethanol, 2-propoxyethanol, 2-butoxyethanol, 1,2-diacetoxyacetone, acetylacetone, diacetone alcohol, methyl acetoacetate, N-methylpyrrolidone, propylene glycol monomethyl ether acetate, and ethyl acetoacetate.

Examples of the crosslinking agent included in the coating solution for forming a layer c include a polyisocyanate compound (preferably a diisocyanate compound), a silane coupling agent, a titanium coupling agent, a polyepoxy compound, a polyamine compound, and a melamine compound.

The thickness of the layer c is preferably 0.1 to 100 μm, more preferably 0.5 to 50 μm, and further preferably 1 to 10 μm.

The medical lubricating member according to an embodiment of the present invention is preferably used as a member of a medical device. The medical lubricating member according to an embodiment of the present invention is normally used such that the layer c serves as an outermost surface of the medical device (in a tubular medical device, at least one of an inner surface of a tube or an outer surface of a tube).

In the present invention, the medical device is not particularly limited. Examples of the medical device include a medical tube, a guide wire, an endoscope, a surgical needle, a surgical suture, forceps, an artificial blood vessel, an artificial heart, and a contact lens. In particular, the medical device to which the medical lubricating member according to an embodiment of the present invention is applied is preferably an endoscope, a guide wire, a medical tube, or a surgical needle from the viewpoint of effectively utilizing the slidability of the medical lubricating member according to an embodiment of the present invention in a wet state.

EXAMPLES

Hereafter, the present invention will be further described in detail based on Examples. The present invention should not be construed as being limited to Examples.

1. Preparation of Polymer Solution

Synthesis Example 1

To a reaction apparatus equipped with a reflux column and a stirrer, 16.0 g of silicone macromer AK-32 (trade name, manufactured by Toagosei Co., Ltd., number-average molecular weight: 20,000), 4.0 g of hydroxyethyl methacrylate (manufactured by Tokyo Chemical Industry Co., Ltd.), 10.0 g of methoxy polyethylene glycol methacrylate (hereafter referred to as MPEGA) (manufactured by Aldrich, number-average molecular weight: 5,000), 10.0 g of methyl methacrylate (manufactured by Tokyo Chemical Industry Co., Ltd.), 0.03 g of azobisisobutyronitrile (AIBN) (manufactured by Wako Pure Chemical Industries, Ltd.), and 60 g of methyl ethyl ketone (MEK) (manufactured by Wako Pure Chemical Industries, Ltd.) were added, and stirring was performed at 80° C. for 20 hours to cause a polymerization reaction. The obtained reaction solution was used as a polymer solution A-1. The weight-average molecular weight of the polymer in the polymer solution A-1 was 20,000.

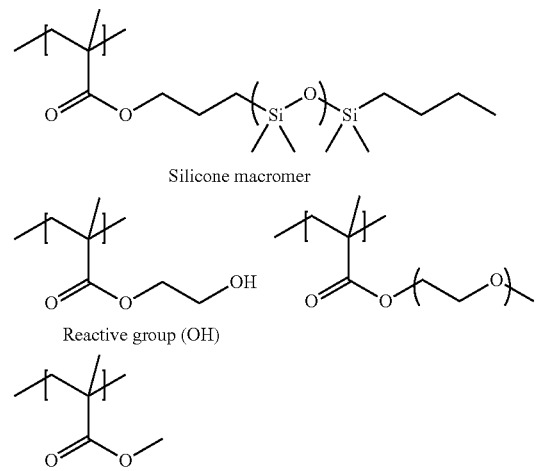

Silicone macromer

Reactive group (OH)

Synthesis Example 2

A polymer solution A-2 was prepared in the same manner as in Synthesis Example 1, except that 4.0 g of acrylic acid (manufactured by Tokyo Chemical Industry Co., Ltd.) was used instead of 4.0 g of hydroxyethyl methacrylate (manufactured by Tokyo Chemical Industry Co., Ltd.) in Synthesis Example 1. The weight-average molecular weight of the polymer in the polymer solution A-2 was 30,000.

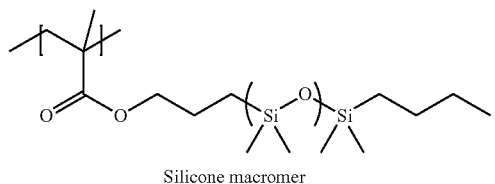

Silicone macromer

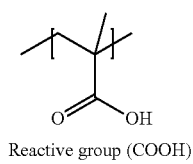
Reactive group (COOH)

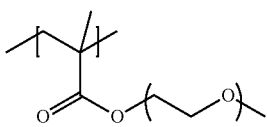

Synthesis Example 3

A polymer solution 3 was prepared in the same manner as in Synthesis Example 1, except that 6.0 g of 2-(dimethylamino)ethyl methacrylate (manufactured by Tokyo Chemical Industry Co., Ltd.) was used instead of 4.0 g of hydroxyethyl methacrylate in Synthesis Example 1, and the amount of the methyl methacrylate was changed to 8.0 g. The weight-average molecular weight of the polymer in the polymer solution 3 was 22,000.

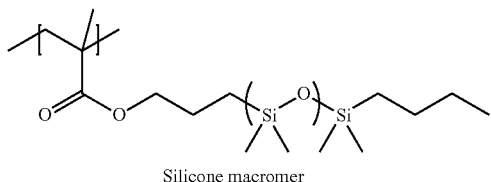
Silicone macromer

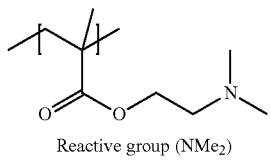
Reactive group (NMe$_2$)

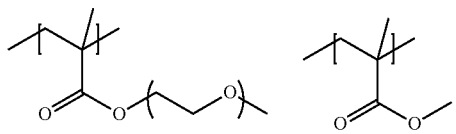

TABLE 1

|  |  | Polymer solution | | |
|---|---|---|---|---|
|  |  | A-1 | A-2 | A-3 |
| Monomer (1) | Silicone macromer AK-32 | 16.0 | 16.0 | 16.0 |
| Monomer (2) | Hydroxyethyl methacrylate | 4.0 | — | — |
|  | Acrylic acid | — | 4.0 | — |
|  | 2-(Dimethylamino)ethyl methacrylate | — | — | 6.0 |
|  | MPEGA | 10.0 | 10.0 | 10.0 |
|  | Methyl methacrylate | 10.0 | 10.0 | 8.0 |

TABLE 1-continued

|  |  | Polymer solution | | |
|---|---|---|---|---|
|  |  | A-1 | A-2 | A-3 |
| Polymerization initiator | Azobisisobutyronitrile | 0.03 | 0.03 | 0.03 |
| Solvent | Methyl ethyl ketone | 60 | 60 | 60 |
| Total |  | 100.03 | 100.03 | 100.03 |

Note in Table
Silicone macromer AK-32: manufactured by Toagosei Co., Ltd., number-average molecular weight: 20,000, having a structural unit represented by formula (1)
MPEGA: methoxy polyethylene glycol methacrylate, manufactured by Aldrich, number-average molecular weight: 5,000

2. Preparation of Undercoat Layer (Layer b)

Components selected from each of the polymer solution (A), the crosslinking agent (B), the catalyst for crosslinking reaction (C), the filler (D), the film-forming aid (E), and the viscosity modifier (F) were dissolved in the solvent (G) in amounts shown in Tables 2-1 to 2-3 below to prepare undercoating solutions used in Examples 1 to 23 and Comparative Examples 1 to 5. In Tables 2-1 to 2-3, the amount is expressed in units of g, the amount of the polymer solution (A) is a mass in the form of solution, and "-" means that the corresponding component is not contained.

3. Preparation of Hydrophilic Coating Solution (1) Hydrophilic Coating Solution 1

A hydrophilic coating solution 1 was prepared by dissolving 2.0 g of polyvinylpyrrolidone (K-90 (trade name), manufactured by Wako Pure Chemical Industries, Ltd.) and 0.25 g of 4,4 diphenylmethane diisocyanate (MDI) (manufactured by Tokyo Chemical Industry Co., Ltd.) in 100 g of chloroform.

(2) Hydrophilic Coating Solution 2

A hydrophilic coating solution 2 was prepared by dissolving 2.0 g of a maleic anhydride-vinyl ether copolymer (number-average molecular weight: 311,000, manufactured by Aldrich) in 100 g of chloroform.

4. Production of Sheet with Hydrophilic Lubricating Coating Layer (Layer c)

Example 1

A silicone rubber sheet (trade name: KE-880-U, hardness: 80 A, manufactured by Shin-Etsu Chemical Co., Ltd., surface free energy: 22 mN/m) having a thickness of 500 μm, a width of 50 mm, and a length of 50 mm was immersed in the undercoating solution shown in Table 2-1 for 3 minutes and then dried by heating at 150° C. for 30 minutes. The dried sheet was immersed in a 10% aqueous hydrochloric acid solution for 12 hours or longer, then washed with methanol, and air-dried at room temperature for 1 hour. The air-dried sheet was immersed in the hydrophilic coating solution 1 for 3 minutes, and subsequently dried by heating at 60° C. for 30 minutes and then at 135° C. for 30 minutes to form a hydrophilic lubricating coat, thereby producing a sheet with a hydrophilic lubricating coating layer (hereafter referred to as a "sheet with a hydrophilic coating layer").

Examples 2 to 21

Sheets with a hydrophilic coating layer in Examples 2 to 21 were produced in the same manner as in Example 1, except that the undercoating solutions in Examples 2 to 21 each having a composition shown in Tables 2-1 to 2-3 were used instead of the undercoating solution in Example 1.

Example 22

A sheet with a hydrophilic coating layer in Example 22 was produced in the same manner as in Example 17, except that a urethane sheet (Shore A hardness: 80) having a composition shown in Table 2-3 was used instead of the silicone rubber sheet in Example 1.

Example 23

A sheet with a hydrophilic coating layer in Example 23 was produced in the same manner as in Example 17, except that the hydrophilic coating solution 2 having a composition shown in Table 2-3 was used instead of the hydrophilic coating solution 1 in Example 1.

Comparative Examples 1 to 5

Sheets with a hydrophilic coating layer in Comparative Examples 1 to 5 were produced in the same manner as in Example 1, except that the undercoating solutions in Comparative Examples 1 to 5 were used instead of the undercoating solution in Example 1.

Test

The sheet with a hydrophilic coating layer prepared above was subjected to the following tests. Tables 2-1 to 2-3 collectively show the test results.

Slidability

The slidability in a wet state was evaluated with a continuous load type scratch resistance tester TYPE: 18 type (manufactured by HEIDON). Friction was applied to the hydrophilic coating layer of the obtained sheet with a hydrophilic coating layer by moving a tetrafluoroethylene indenter back and forth once at a load of 500 g under water immersion to measure a dynamic friction coefficient ($\mu k$), and the slidability was evaluated on the basis of evaluation criteria below. "A" to "C" are acceptable levels in this test.

Evaluation Criteria

A: $\mu k \leq 0.03$
B: $0.03 < \mu k \leq 0.06$
C: $0.06 < \mu k \leq 0.1$
D: $0.1 < \mu k$ Adhesiveness The surface of the hydrophilic coating layer of the obtained sheet with a hydrophilic coating layer was subjected to a cross-cut test in conformity with JIS K5600-5-6 (1999). The test area was classified into six grades of classes 0 to 5 described in JIS K5600-5-6, and evaluated on the basis of the following criteria. "A" to "C" are acceptable levels in this test.

Evaluation Criteria

A: class 0
B: class 1
C: class 2 or 3
D: class 4 or 5

Layer Uniformity

Ten sheets with a hydrophilic coating layer were produced as samples by the above production method. The thickness of the undercoat layer was measured at five positions for each sample, that is, at 50 positions in total using "Spectroscopic ellipsometer UVISEL2" (trade name) manufactured by Horiba, Ltd. Herein, the five positions are the center of the square sample surface having a size of 50 mm×50 mm and four intermediate positions between the center and each corner.

The relative standard deviation was calculated by setting the number n of measured values to 50, and the evaluation was made on the basis of the following criteria. In all cases, "A" to "C" are acceptable levels in this test.

Evaluation Criteria

A: The relative standard deviation is 20% or less.
B: The relative standard deviation is more than 20% and 30% or less.
C: The relative standard deviation is more than 30% and 40% or less.
D: The relative standard deviation is more than 40%.

Crack Resistance (Heat Resistance)

The obtained sheet with a hydrophilic coating layer was heated for 10 minutes in an oven heated to 150° C. in advance. Immediately after taking out the sheet, the sheet was placed on a stainless plate at 23° C. so that the coating layer faced upward, and air-cooled for 1 hour. After the air-cooling, the surface of the coating layer was visually observed for the presence or absence of cracks and evaluated on the basis of the following criteria. "A" to "C" are acceptable levels in this test.

Evaluation Criteria

A: No cracks are observed at all.
B: Cracks are slightly observed (within two cracks per sheet).
C: Cracks are observed in a wide area (three or more and six or less cracks per sheet).
D: Cracks are considerably observed on the whole (seven or more cracks per sheet).

Bending Resistance

When the obtained sheet with a hydrophilic coating layer was rolled up while the hydrophilic coating layer was present inside, the diameter of curvature R at which a crack was first formed in the coating layer was evaluated on the basis of the following criteria. "A" to "C" are acceptable levels in this test.

Evaluation Criteria

A: $R \leq 20$ mm
B: 20 mm $< R \leq 50$ mm
C: 50 mm $< R \leq 100$ mm
D: 100 mm $< R$ Chemical Resistance Twenty-five cycles of ethylene oxide sterilization treatment (ethylene oxide gas concentration: 100%, humidity: 70% $R^H$, time: 2 hours and 45 minutes) were performed on the obtained sheet with a hydrophilic coating layer. The lightness $L^*(L)$ was measured using a colorimeter ("CM-700d" manufactured by Konica Minolta, Inc.). For the degree of whitening, the difference ($\Delta L = L_0 - L$) from the lightness $L^*(L_0)$ of the sheet with a hydrophilic coating layer before the treatment was determined, and evaluated on the basis of the following criteria. "A" to "C" are acceptable levels in this test.

Evaluation Criteria

A: $\Delta L \leq 3$
B: $3 < \Delta L \leq 5$
C: $5 < \Delta L \leq 10$
D: $10 < \Delta L$

TABLE 2-1

|  |  | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Polymer solution (A) | Type | A-1 | A-2 | A-3 | A-1 | A-1 | A-1 | A-1 | A-1 | A-1 | A-1 |
|  | Amount | 6.3 | 6.3 | 6.3 | 6.3 | 6.3 | 6.3 | 6.3 | 6.3 | 6.3 | 6.3 |
| Crosslinking agent (B) | Type | B-1 | B-1 | B-1 | B-1 | B-1 | B-1 | B-1 | B-1 | B-1 | B-1 |
|  | Amount | 6.3 | 6.3 | 6.3 | 6.3 | 6.3 | 6.3 | 6.3 | 6.3 | 6.3 | 6.3 |
| Catalyst for crosslinking reaction (C) | Type | C-1 | C-1 | C-1 | C-2 | C-3 | C-4 | C-5 | C-1 | C-1 | C-1 |
|  | Amount | 0.2 | 0.2 | 0.2 | 0.2 | 0.2 | 0.2 | 0.2 | 0.2 | 0.2 | 0.2 |
| Filler (D) | Type | — | — | — | — | — | — | — | D-1 | D-2 | D-3 |
|  | Amount |  |  |  |  |  |  |  | 10 | 10 | 10 |
| Film-forming aid (E) | Type | — | — | — | — | — | — | — | — | — | — |
|  | Amount |  |  |  |  |  |  |  |  |  |  |
| Viscosity modifier (F) | Type | — | — | — | — | — | — | — | — | — | — |
|  | Amount |  |  |  |  |  |  |  |  |  |  |
| Solvent (G) | Type | IPA | IPA | IPA | IPA | IPA | IPA | IPA | IPA | IPA | IPA |
|  | Amount | 87.2 | 87.2 | 87.2 | 87.2 | 87.2 | 87.2 | 87.2 | 77.2 | 77.2 | 77.2 |
| Substrate a |  | Silicone | Silicone | Silicone | Silicone | Silicone | Silicone | Silicone | Silicone | Silicone | Silicone |
| Slidability |  | A | A | A | A | A | A | A | A | A | A |
| Adhesiveness |  | A | A | B | A | A | A | A | A | A | A |
| Layer uniformity |  | C | C | C | C | C | C | C | C | C | C |
| Heat resistance |  | C | C | C | C | C | C | C | A | A | B |
| Bending resistance |  | C | C | C | C | C | C | C | C | C | C |
| Chemical resistance |  | A | B | A | A | A | B | C | A | A | A |

Examples 1 to 10: with a layer c formed from the hydrophilic coating solution 1

TABLE 2-2

|  |  | Example 11 | Example 12 | Example 13 | Example 14 | Example 15 | Example 16 | Example 17 | Example 18 | Example 19 | Example 20 |
|---|---|---|---|---|---|---|---|---|---|---|---|
| Polymer solution (A) | Type | A-1 | A-1 | A-1 | A-1 | A-1 | A-1 | A-1 | A-1 | A-1 | A-1 |
|  | Amount | 6.3 | 6.3 | 6.3 | 6.3 | 6.3 | 6.3 | 6.3 | 6.3 | 6.3 | 6.3 |
| Crosslinking agent (B) | Type | B-1 | B-1 | B-1 | B-1 | B-1 | B-1 | B-1 | B-1 | B-2 | B-1 |
|  | Amount | 6.3 | 6.3 | 6.3 | 6.3 | 6.3 | 6.3 | 6.3 | 6.3 | 2.5 | 6.3 |
| Catalyst for crosslinking reaction (C) | Type | C-1 | C-1 | C-1 | C-1 | C-1 | C-1 | C-1 | C-1 | C-1 | C-1 |
|  | Amount | 0.2 | 0.2 | 0.2 | 0.2 | 0.2 | 0.2 | 0.2 | 0.2 | 0.2 | 0.2 |
| Filler (D) | Type | D-4 | D-5 | D-1 | D-1 | D-1 | D-1 | D-1 | D-1 | D-1 | — |
|  | Amount | 10 | 10 | 10 | 10 | 10 | 10 | 10 | 10 | 10 |  |
| Film-forming aid (E) | Type | — | — | E-1 | E-2 | E-3 | E-4 | E-1 | E-1 | E-1 | E-1 |
|  | Amount |  |  | 1 | 1 | 1 | 1 | 1 | 1 | 1 | 1 |
| Viscosity modifier (F) | Type | — | — | — | — | — | — | F-1 | F-2 | F-1 | — |
|  | Amount |  |  |  |  |  |  | 3.5 | 3.5 | 3.5 |  |
| Solvent (G) | Type | IPA | IPA | IPA | IPA | IPA | IPA | IPA | IPA | IPA | IPA |
|  | Amount | 77.2 | 77.2 | 76.2 | 76.2 | 76.2 | 76.2 | 72.7 | 72.7 | 76.5 | 86.2 |
| Substrate a |  | Silicone | Silicone | Silicone | Silicone | Silicone | Silicone | Silicone | Silicone | Silicone | Silicone |
| Slidability |  | A | A | A | A | A | A | A | A | A | A |
| Adhesiveness |  | A | A | A | A | A | A | A | A | A | A |
| Layer uniformity |  | C | C | A | A | B | C | A | A | A | A |
| Heat resistance |  | B | C | A | A | A | A | A | A | B | C |
| Bending resistance |  | C | C | C | C | C | C | A | A | B | C |
| Chemical resistance |  | A | A | A | A | A | A | A | A | A | A |

Examples 11 to 20: with a layer c formed from the hydrophilic coating solution 1

TABLE 2-3

|  |  | Example 21 | Example 22 | Example 23 | Comparative Example 1 | Comparative Example 2 | Comparative Example 3 | Comparative Example 4 | Comparative Example 5 |
|---|---|---|---|---|---|---|---|---|---|
| Polymer solution (A) | Type | A-1 | A-1 | A-1 | A-1 | A-1 | A-1 | A-1 | A-1 |
|  | Amount | 6.3 | 6.3 | 6.3 | 6.3 | 12.6 | 6.3 | 6.3 | 12.6 |
| Crosslinking agent (B) | Type | B-1 | B-1 | B-1 | B-1 | — | B-3 | B-1 | — |
|  | Amount | 6.3 | 6.3 | 6.3 | 6.3 |  | 2.5 | 6.3 |  |

TABLE 2-3-continued

|  |  | Example 21 | Example 22 | Example 23 | Comparative Example 1 | Comparative Example 2 | Comparative Example 3 | Comparative Example 4 | Comparative Example 5 |
|---|---|---|---|---|---|---|---|---|---|
| Catalyst for crosslinking reaction (C) | Type | C-1 | C-1 | C-1 | — | — | C-1 | — | — |
|  | Amount | 0.2 | 0.2 | 0.2 |  |  | 0.2 |  |  |
| Filler (D) | Type | — | D-1 | D-1 | — | — | — | D-1 | D-1 |
|  | Amount |  | 10 | 10 |  |  |  | 10 | 10 |
| Film-forming aid (E) | Type | — | E-1 | E-1 | — | — | — | E-1 | E-1 |
|  | Amount |  | 1 | 1 |  |  |  | 1 | 1 |
| Viscosity modifier (F) | Type | F-1 | F-1 | F-1 | — | — | — | F-1 | F-1 |
|  | Amount | 3.5 | 3.5 | 3.5 |  |  |  | 3.5 | 3.5 |
| Solvent (G) | Type | IPA | IPA | IPA | IPA | IPA | IPA | IPA | IPA |
|  | Amount | 83.7 | 72.7 | 72.7 | 87.4 | 87.4 | 91 | 72.9 | 72.9 |
| Substrate a |  | Silicone | Urethane | Silicone | Silicone | Silicone | Silicone | Silicone | Silicone |
| Slidability |  | A | A | A | A | A | A | A | A |
| Adhesiveness |  | A | A | A | A | C | A | A | C |
| Layer uniformity |  | C | A | A | C | D | C | A | B |
| Heat resistance |  | C | A | A | D | D | D | C | C |
| Bending resistance |  | A | A | A | C | D | D | A | B |
| Chemical resistance |  | A | A | A | D | D | A | D | D |

Examples 21 and 22 and Comparative Examples 1 to 5: with a layer c formed from the hydrophilic coating solution 1
Example 23: with a layer c formed from the hydrophilic coating solution 2

Note in Table
Polymer Solution (A)
  Polymer solutions A-1 to A-3: the polymer solutions prepared above, each having a solid content of 40 mass %
Crosslinking Agent (B)
  B-1: oxazoline polymer ("EPOCROS WS-500" (trade name) manufactured by Nippon Shokubai Co., Ltd.)
  B-2: isocyanate ("Coronate HX" (trade name) manufactured by Nippon Polyurethane Industry Co., Ltd.)
  B-3: 4,4'-dibenzoylquinone dioxime (reagent manufactured by Tokyo Chemical Industry Co., Ltd.)
Catalyst for Crosslinking Reaction (C)
  C-1: p-toluenesulfonic acid monohydrate ("PTSA" (trade name) manufactured by Meiyusangyo Co., Ltd.)
  C-2: n-butyl acid phosphate ("JP-504" (trade name) manufactured by Johoku Chemical Co., Ltd.)
  C-3: 2-ethylhexyl acid ("Octylic acid" manufactured by KH Neochem Co., Ltd.)
  C-4: blocked dodecylbenzenesulfonic acid ("NACURE 5525" (trade name) manufactured by Kusumoto Chemicals, Ltd.)
  C-5: magnesium bromide (Lewis acid)
Filler (D)
  D-1: silica ("Aerosil 200" (trade name) manufactured by Nippon Aerosil Co., Ltd., average primary particle size 12 nm)
  D-2: alumina ("Taimicron TM-DA" (trade name) manufactured by Taimei Chemicals Co., Ltd., average primary particle size 0.10 μm)
  D-3: titanium oxide ("A-190" manufactured by Sakai Chemical Industry Co., Ltd., average particle size 0.15 μm)
  D-4: zinc oxide ("FINEX-50-LPT" (trade name) manufactured by Sakai Chemical Industry Co., Ltd., average primary particle size 20 nm)
  D-5: zirconium oxide ("KZ-0Y-LSF" (trade name) manufactured by KCM Corporation, average primary particle size 100 nm)
Film-Forming Aid (E)
  E-1: anionic surfactant (dioctyl sulfosuccinate sodium salt, "SANSEPARER 100" (trade name) manufactured by Sanyo Chemical Industries, Ltd.)
  E-2: nonionic surfactant (sorbitan monooleate, "Rheodol AO-10V" (trade name) manufactured by Kao Corporation)
  E-3: polyether-modified siloxane (PEG9-dimethicone, "KF-6013" (trade name) manufactured by Shin-Etsu Chemical Co., Ltd.)
  E-4: silicone oil ("KF-54" (trade name) manufactured by Shin-Etsu Chemical Co., Ltd.)
Viscosity Modifier (F)
  F-1: cellulose acetate butyrate (CAB resin, "EASTMAN-CAB (trade name)" manufactured by Eastman Chemical Company
  F-2: ethyl acrylate/2-ethylhexyl acrylate copolymer ("Modaflow Powder III" (trade name) manufactured by Nippon Cytec Industries Inc.)
Solvent (G)
IPA: Isopropyl Alcohol As is clear from Tables 2-1 to 2-3, the sheets with a hydrophilic coating layer in Comparative Examples 1 to 5 were inferior in terms of at least one of adhesiveness, layer uniformity, heat resistance, bending resistance, or chemical resistance. The results in Comparative Example 3 show that even when a catalyst for crosslinking reaction is used, the heat resistance and the bending resistance are inferior when a crosslinking agent that is not represented by any of the formulae (CL1) and (CL2) is used.

In contrast, the results in Examples 1 to 23 show that the sheet with a hydrophilic coating layer (medical lubricating member) that meets the requirements of the present invention is excellent in terms of slidability, adhesiveness, layer uniformity, heat resistance, bending resistance, and chemical resistance.

While the present invention has been described with reference to the embodiments thereof, we do not intend to limit our invention in any detail of the description unless otherwise specified. Rather, the invention should be broadly construed without departing from the spirit and scope of the invention as defined by the appended claims.

REFERENCE SIGNS LIST

10 laminated material
20 medical lubricating member
a substrate
b layer including a crosslinked polymer having a polysiloxane structure
c layer including a hydrophilic polymer

What is claimed is:
1. A medical lubricating member comprising:
a laminated material used for a medical lubricating member, the laminated material comprising:
a substrate a; and
a layer b disposed on the substrate a,
wherein the layer b includes a catalyst for crosslinking reaction and a crosslinked polymer including, as a constituent component, a polymer b including a polysiloxane structure,
the polymer b includes, as a constituent component, at least one of an acrylic acid component, an acrylic acid ester component, an acrylamide component, or a styrene component,
the polymer b has at least one of a hydroxy group, a carboxy group, an amino group, an isocyanate group, an oxazolinyl group, an epoxy group, a vinyl group, an ethynyl group, a sulfanyl group, an azide group, a trialkoxysilyl group, or an acid anhydride structure, and
the crosslinked polymer has a crosslinking agent component including at least one of a crosslinking agent having a structural unit represented by formula (CL1) below or a crosslinking agent represented by formula (CL2) below,

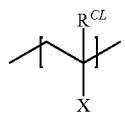

Formula (CL1)

$Y-[R^{dm}]_m$   Formula (CL2)

wherein $R^{CL}$ represents a hydrogen atom or an organic group,
X represents a hydroxy group, a carboxy group, an amino group, an isocyanate group, an oxazolinyl group, an epoxy group, a vinyl group, an ethynyl group, a sulfanyl group, an azide group, a trialkoxysilyl group, or a group having an acid anhydride structure,
Y represents an m-valent linking group,
m represents an integer of 2 or more,
$R^{dm}$ has the same definition as X; and
a layer c that is disposed on the layer b constituting the laminated material and that includes a hydrophilic polymer.
2. The medical lubricating member according to claim 1, wherein, in formula (CL1) or formula (CL2), X or $R^{dm}$ represents an oxazolinyl group.
3. A medical device comprising:
the medical lubricating member according to claim 1,
wherein the medical device is selected from the group consisting of a medical tube, a guide wire, an endoscope, a surgical needle, a surgical suture, forceps, an artificial blood vessel, an artificial heart, and a contact lens.

* * * * *